US010014148B2

(12) United States Patent
Tang et al.

(10) Patent No.: US 10,014,148 B2
(45) Date of Patent: Jul. 3, 2018

(54) ELECTRON SOURCE, X-RAY SOURCE AND DEVICE USING THE X-RAY SOURCE

(71) Applicant: Nuctech Company Limited, Beijing (CN)

(72) Inventors: Huaping Tang, Beijing (CN); Zhiqiang Chen, Beijing (CN); Yuanjing Li, Beijing (CN); Yonggang Wang, Beijing (CN); Zhanfeng Qin, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 14/904,061

(22) PCT Filed: Aug. 19, 2015

(86) PCT No.: PCT/CN2015/087488
§ 371 (c)(1),
(2) Date: Jan. 8, 2016

(87) PCT Pub. No.: WO2016/029811
PCT Pub. Date: Mar. 3, 2016

(65) Prior Publication Data

US 2017/0162359 A1 Jun. 8, 2017

(30) Foreign Application Priority Data

Aug. 25, 2014 (CN) .......................... 2014 1 0419359

(51) Int. Cl.
*A61B 6/03* (2006.01)
*A61B 6/04* (2006.01)
(Continued)

(52) U.S. Cl.
CPC ............ *H01J 35/065* (2013.01); *H01J 35/14* (2013.01); *H01J 2235/062* (2013.01)

(58) Field of Classification Search
CPC ............... H01J 35/065; H01J 2235/068; H01J 2235/062; H01J 35/14; H01J 35/06
See application file for complete search history.

(56) References Cited

U.S. PATENT DOCUMENTS 4,165,472 A 8/1979 Wittry
4,721,885 A 1/1988 Brodie
(Continued)

FOREIGN PATENT DOCUMENTS

CN 101452797 A 6/2009
CN 101452797 A 6/2009
(Continued)

OTHER PUBLICATIONS

Chinese First Office Action and Search Report dated Nov. 2, 2016 in Chinese Application No. 201410419359.2, and English-language summary/translation of same; 14 pages.
(Continued)

*Primary Examiner* — Don Wong
(74) *Attorney, Agent, or Firm* — Knobbe Martens Olson & Bear, LLP

(57) ABSTRACT

The present disclosure is directed to an electron source and an X-ray source using the same. The electron source of the present invention comprises: at least two electron emission zones, each of which comprises a plurality of micro electron emission units, wherein the micro electron emission unit comprises: a base layer, an insulating layer on the base layer, a grid layer on the insulating layer, an opening in the grid layer, and an electron emitter that is fixed at the base layer and corresponds to a position of the opening, wherein the micro electron emission units in the same electron emission zone are electrically connected and simultaneously emit
(Continued)

electrons or do not emit electrons at the same time, and wherein different electron emission zones are electrically partitioned.

20 Claims, 10 Drawing Sheets

(51) Int. Cl.

| | |
|---|---|
| ***H01J 37/26*** | (2006.01) |
| ***H01J 35/06*** | (2006.01) |
| ***H01J 35/14*** | (2006.01) |

(56) References Cited

U.S. PATENT DOCUMENTS

| | | | | |
|---|---|---|---|---|
| 5,176,557 | A | 1/1993 | Okunuki et al. | |
| 5,604,401 | A | 2/1997 | Makishima | |
| 5,773,921 | A | 6/1998 | Keesmann et al. | |
| 6,031,328 | A | 2/2000 | Nakamoto | |
| 6,385,288 | B1 | 5/2002 | Kanematsu | |
| 7,555,099 | B2 | 6/2009 | Rothschild et al. | |
| 8,350,459 | B2 | 1/2013 | Qian et al. | |
| 2007/0053489 | A1 | 3/2007 | Lu et al. | |
| 2009/0316860 | A1 | 12/2009 | Okunuki et al. | |
| 2010/0019166 | A1* | 1/2010 | Kim | B82Y 10/00 250/396 R |
| 2010/0310051 | A1 | 12/2010 | Tsujii et al. | |
| 2014/0010347 | A1 | 1/2014 | Kim et al. | |
| 2014/0133629 | A1 | 5/2014 | Morton | |

FOREIGN PATENT DOCUMENTS

| | | | |
|---|---|---|---|
| CN | 101940066 | A | 1/2011 |
| CN | 101940066 | A | 1/2011 |
| CN | 101961530 | A | 2/2011 |
| CN | 102074429 | A | 5/2011 |
| CN | 102306595 | | 1/2012 |
| CN | 103400739 | | 11/2013 |
| CN | 103400739 | A | 11/2013 |
| CN | 203563254 | U | 4/2014 |
| JP | H01502307 | | 8/1989 |
| JP | H07-182968 | A | 7/1995 |
| JP | 2000-340121 | | 12/2000 |
| JP | 2000-348603 | | 12/2000 |
| JP | 2002-157953 | A | 5/2002 |
| JP | 2007-305493 | A | 11/2007 |
| KR | 20080032532 | | 4/2008 |
| KR | 20110005726 | | 1/2011 |
| RU | 135214 | U1 | 11/2013 |

OTHER PUBLICATIONS

Japanese Office Action dated Dec. 6, 2016 in related Application No. 2016-544723, and English-language translation of same; 6 pages.

Heo, Sung Hwan, et al., "Transmission-type microfocus x-ray tube using carbon nanotube field emitters," Applied Physics Letters 90, 183109 (2007); 3 pages.

Office Action dated Jan. 31, 2017 in related Canadian Patent Application No. 2,919,744; 8 pages.

Office Action dated Jul. 24, 2017 in Korean Patent Application No. 10-2016-7010573 (4 pgs), and English-language translation of Office Action (2 pgs); 6 pages total.

Office Action dated Jul. 7, 2017 in Japanese Patent Application No. JP2016-544723 (3 pgs), and English-language translation of Office Action (2 pgs); 5 pages total.

Office Action dated May 19, 2017 in Chinese Application No. 2014104193592 (12 pgs), and English-language translation of Office Action (2 pgs); 14 pages total.

International Search Report, PCT/CN2015/087488, dated Oct. 29, 2015; 5 pages.

Office Action and Search Report dated Nov. 16, 2017, in Chinese Application No. 201410419359.2 (15 pgs), and concise English-language explanation/summary thereof (2 pgs); 17 pages total.

Office Action dated Aug. 21, 2017 received in Chinese Application No. 201410419359.2, (15 pgs) and concise English-language summary of same (2 pgs); 17 pgs. total Office Action dated Apr. 24, 2018, in Russian Patent Application No. 2016102389/07 (7 pgs.), and English-language translation of same (2 pgs.); 9 pages total.

Supplementary Partial Search Report dated Mar. 16, 2018 in European Patent Application No. 15813227.4; 17 pages.

* cited by examiner

ELECTRON SOURCE, X-RAY SOURCE AND DEVICE USING THE X-RAY SOURCE

CROSS-REFERENCE TO RELATED APPLICATIONS

This application claims priority to PCT Application No. PCT/CN2015/087488, filed Aug. 19, 2015, published as WO2016/029811A1, entitled "Electron Source, X-Ray source and Device Using the X-Ray Source", and to Chinese Patent Application No. 201410419359.2, filed on Aug. 25, 2014, published as CN105374654A, which are incorporated herein by reference in their entirety.

FIELD OF THE INVENTION

The present disclosure relates to an electron source for generating electron beam currents and an X-ray source for generating X-rays by using the electron source, particularly to an electron source for generating electron beam currents from different locations in a predetermined manner, an X-ray source for generating X-rays from different locations in a predetermined manner and a device using the X-ray source.

BACKGROUND

An electron source is a device or component capable of generating electron beam currents, often called electron gun, cathode, emitter, etc. Electron sources are widely used in displays, X-ray sources, microwave tubes, etc. An X-ray source is a device that generates X-ray. The core part of the X-ray source is an X-ray tube. The X-ray source comprises an electron source, an anode and a vacuum seal housing, and usually further comprising a power supply, a control system and auxiliary components, such as a cooling, a shield and so on. The X-ray source is widely used in industrial nondestructive testing, security check, medical diagnosis and treatment, etc.

Traditionally, an X-ray source adopts a direct cooling tungsten filament as the cathode. During operation, the filament through which an electric current flows is heated to an operating temperature of about 2000K and then generates an electron beam current through thermal emission. The electron beam current is accelerated by an electric field at hundreds of thousands of voltage between the anode and the cathode toward the anode, strikes a target and then generates an X-ray.

Field emission can be caused by a plurality of materials, such as metal needle, carbon nano-tube, etc., to emit electrons at room temperature and generate electron beam currents. After the development of nanotechnology, especially carbon nano-material, field emission electron sources with nano-materials grow quickly.

An X-ray source requires its electron source to have a large emission current, usually larger than 1 mA. For example, in existing medical CTs, oil-cooled X-ray sources with rotating targets can emit an electric current of up to 1300 mA. As disclosed in Patent Reference 1, in an existing X-ray device which adopts a field emission electron source with nano-material as cathode, in order to obtain a large emission electric current, a cathode emission surface with a macro size is formed from nano-material, and a mesh grid is arranged above and in parallel with the emission surface to control the field emission. In such structure, due to machining accuracy, deformation of the mesh and installation accuracy, there is a large distance between the mesh grid and the cathode surface, thus the grid needs a very high voltage, normally larger than 1000V, to control the field emission.

Usually, electron emission units using the field emission principle have the substantially same structure, for example, as shown in parts (A), (B) and (C) of FIG. 3. Part (A) of FIG. 3 shows the technical solution disclosed in Patent Reference 2, wherein a nano-material 31 is adhered to a structure 13 of a substrate 10. Part (B) of FIG. 3 shows the technical solution disclosed in Patent Reference 3, wherein a nano-material 20 is directly formed on flat surfaces of substrates 12 and 14. Part (C) of FIG. 3 shows the technical solution disclosed in Patent Reference 4, wherein an electron source for an X-ray source device comprises a nano-material surface 330 with a micro size (millimeters to centimeters), and its grid is a mesh grid with a micro size, and the grid surface is parallel to the nano-material surface.

Patent Reference 1: CN102870189B;
Patent Reference 2: U.S. Pat. No. 5,773,921;
Patent Reference 3: U.S. Pat. No. 5,973,444; and
Patent Reference 4: CN100459019.

SUMMARY OF THE INVENTION

An aspect of the present invention provides a field emission electron source that has a novel structure, for purpose of achieving simple structure, low cost, low control voltage and large intensity of emission current. It is also provided an X-ray source using the electron source, which has a large output intensity of X-ray and a low cost, or getting a number of X-ray target spots at different positions, wherein the target spot have a large beam intensity and a small gap.

An aspect of the present invention provides a field emission electron source that has a low control voltage and a large emission current and an X-ray source using the electron source. The electron source of the present invention comprises at least two electron emission zones, each of which comprises a plurality of micro electron emission units. The structure of the micro electron emission unit in the present invention enables a very low control voltage for field emission. The combined operation of numerous electron emission units provides the electron emission zone with a large emission current. The X-ray source using the electron source may be designed as a dual-energy X-ray source by means of the design for the anode. Through the design for the electron source, a distributed X-ray source with a plurality of target spots at different locations can be achieved. Multiple operation modes can improve an output intensity of X-ray at each target spot, reduce gaps between the targets, avoid black spots, and extend functions and applications of the distributed X-ray source for field emission. Moreover, by reducing control voltage, it is possible to facilitate control of the system and reduce production cost and malfunction, thereby extending life of the distributed X-ray source.

Furthermore, an aspect of the present invention further provides applications of the above distributed X-ray source into X-ray transmission imaging system and back scattering imaging system. Various technical solutions using the X-ray source show one or more advantages, including low cost, fast detection speed, high quality imaging, etc.

Furthermore, an aspect of the present invention further provides real-time image-guided radiotherapy system. Regarding therapy of body parts having physiological movements, for example lung, heart and so on, the "real-time" image-guided radiotherapy can decrease exposure doses and reduce exposure to normal organics, which is very important. Moreover, the distributed X-ray source of the present invention has a number of target spots and thus can obtain "three-dimensional" diagnostic images having depth information, which differ from normal planar images. In the image-guided radiotherapy, this can further improve the guiding accuracy and locating precision of the radiation beams for radiotherapy.

To achieve objects of the present invention, the following technical solutions are adopted.

An aspect of the present invention provides an electron source, comprising: at least one electron emission zone, which comprises a plurality of micro electron emission units, wherein the micro electron emission unit comprises: a base layer, an insulating layer on the base layer, a grid layer on the insulating layer, an opening in the grid layer, and an electron emitter that is fixed at the base layer and corresponds to a position of the opening, and wherein all the micro electron emission units in the electron emission zone simultaneously emit electrons or do not emit electrons at the same time.

Furthermore, in the present invention, the base layer may be used to provide structural support and electrical connection.

Furthermore, in the present invention, the grid layer may be made of conductive materials.

Furthermore, in the present invention, the opening may penetrate through the grid layer and the insulating layer and reaches the base layer.

Furthermore, in the present invention, the insulating layer may have a thickness less than 200 μm.

Furthermore, in the present invention, the opening may have a size that is less than the thickness of the insulating layer.

Furthermore, in the present invention, the opening may have a size that is less than a distance from the electron emitter to the grid layer.

Furthermore, in the present invention, the electron emitter may have a height that is less than half of a thickness of the insulating layer.

Furthermore, in the present invention, the electron emitter may be formed to comprise nano-materials.

Furthermore, in the present invention, the grid layer may be parallel to the base layer.

Furthermore, in the present invention, the micro electron emission unit may occupy a spatial size at a micrometer level along an array arrangement direction. Preferably, the spatial size occupied by the micro electron emission unit along an array arrangement direction may be ranged from 1 μm to 200 μm.

Furthermore, in the present invention, a ratio of a length to a width of the electron emission zone may be larger than 2.

Furthermore, in the present invention, the base layer may comprise a substrate layer and a conducting layer on the substrate layer, and the electron emitter may be fixed at the conducting layer.

Furthermore, in the present invention, an emission current of each electron emission zone may be not smaller than 0.8 mA.

Furthermore, an aspect of the present invention provides an electron source, comprising: at least two electron emission zones, each of which comprises a plurality of micro electron emission units, wherein the micro electron emission unit comprises: a base layer for providing structural support and electrical connection, an insulating layer on the base layer, a grid layer on the insulating layer made of a conductive material, an opening that penetrates through the grid layer and the insulating layer and reaches the base layer, and an electron emitter fixed at the base layer within the opening, wherein all the micro electron emission units in the same electron emission zone are electrically connected, and simultaneously emit electrons or do not emit electrons at the same time, and wherein different electron emission zones are electrically partitioned.

Furthermore, in the present invention, the insulating layer may have a thickness less than 200 μm.

Furthermore, in the present invention, the grid layer may be parallel to the base layer.

Furthermore, in the present invention, different electron emission zones are electrically partitioned means that: the respective base layers of all the electron emission zones are separated from each other, or the respective grid layers of all the electron emission zones are separated from each other, or both the respective base layers and grid layers of all the electron emission zones are separated from each other.

Furthermore, in the present invention, different electron emission zones can be controlled to emit electrons at a predetermined sequence, such as emitting electrons successively, at intervals, alternatively, partially at the same time, group by group, or in other emission ways.

Furthermore, in the present invention, the respective base layers of all the micro electron emission units in the same electron emission zone may be the same substantive layer, the respective grid layers of all the micro electron emission units may be the same substantive layer, and the respective insulating layers of all the micro electron emission units may be the same substantive layer.

Furthermore, in the present invention, a size of the micro electron emission unit in the electron emission zone along an array arrangement direction can be in a micrometer level.

Furthermore, in the present invention, a spatial size occupied by the micro electron emission unit along an array arrangement direction may be ranged from 1 μm to 200 μm.

Furthermore, in the present invention, the opening may have a size that is less than the thickness of the insulating layer.

Furthermore, in the present invention, the opening may have a size that is less than a distance from the electron emitter to the grid layer.

Furthermore, in the present invention, the electron emitter may have a height that is less than half of a thickness of the insulating layer.

Furthermore, in the present invention, a linear length of the electron emitter may be perpendicular to a surface of the base layer.

Furthermore, in the present invention, the electron emitter may be formed to comprise nano-materials.

Furthermore, in the present invention, the nano-materials may comprise single-walled carbon nano-tubes, double-walled carbon nano-tubes, multi-walled carbon nano-tubes, or any combination thereof.

Furthermore, in the present invention, the base layer may comprise a substrate layer and a conducting layer on the substrate layer. The base layer may be used to provide structural support. The conducting layer may be used to form electrical connection between the respective base layers (fixed electrode of nano-materials) of all the micro electron emission units in the same electron emission zone.

Furthermore, in the present invention, a ratio of a length to a width of the electron emission zone may be larger than 2.

Furthermore, in the present invention, the respective electron emission zones may have a same size, and may be arranged along their short edges in a parallel, aligned and uniform manner.

Furthermore, in the present invention, an emission current of each electron emission zone may be larger than 0.8 mA.

Furthermore, an aspect of the present invention provides an X-ray source, comprising: a vacuum chamber; an electron source disposed within the vacuum chamber; an anode disposed opposite to the electron source within the vacuum chamber; an electron source control device adapted to apply voltage between the base layer and the grid layer of the electron emission zone of the electron source; and a high voltage power supply connected to the anode and adapted to provide high voltage to the anode. The X-ray source is characterized in that: the electron source comprises at least one electron emission zone, which comprises a plurality of micro electron emission units; wherein each micro electron emission unit occupies a spatial size at a micrometer level along an array arrangement direction; wherein the micro electron emission unit comprises: a base layer for providing structural support and electrical connection, an insulating layer on the base layer, a grid layer on the insulating layer made of a conductive material, an opening that penetrates through the grid layer and the insulating layer and reaches the base layer, and an electron emitter fixed at the base layer within the opening; and wherein all the micro electron emission units in the electron emission zone simultaneously emit electrons or do not emit electrons at the same time.

Furthermore, in the present invention, the insulating layer may have a thickness less than 200 μm.

Furthermore, in the present invention, the electron source control device may apply a control voltage for field emission that is less than 500V to the electron source.

Furthermore, an aspect of the present invention provides a distributed X-ray source, comprising: a vacuum chamber; an electron source disposed within the vacuum chamber; an anode disposed opposite to the electron source within the vacuum chamber; an electron source control device adapted to apply voltage between the base layer and the grid layer of the electron emission zone of the electron source; and a high voltage power supply connected to the anode and adapted to provide high voltage to the anode. The X-ray source is characterized in that: the electron source comprises at least two (a number of N) electron emission zones, each of which comprises a plurality of micro electron emission units; wherein the micro electron emission unit comprises: a base layer, an insulating layer on the base layer, a grid layer on the insulating layer, an opening in the grid layer, and an electron emitter fixed at the base layer corresponding to a position of the opening; and wherein all the micro electron emission units in the same electron emission zone are electrically connected, and simultaneously emit electrons or do not emit electrons at the same time; and wherein different electron emission zones are electrically partitioned.

Furthermore, in the present invention, between different electron emission zones of the electron source, the respective base layers may be electrically partitioned, and each base layer may be connected to the electron source control device through a separate lead.

Furthermore, in the present invention, between different electron emission zones of the electron source, the respective grid layers may be electrically partitioned, and each grid layer may be connected to the electron source control device through a separate lead.

Furthermore, in the present invention, a surface of the anode and a surface of the electron source may be opposite to each other, have similar shapes and sizes, maintained in a parallel or substantially parallel relation, and may generate at least two target spots at different locations.

Furthermore, in the present invention, the anode may comprise at least two different materials and may generate X-rays with different comprehensive energies from different target spots.

Furthermore, in the present invention, the electron emission zones in a number of N may have strip shapes, and may be linearly arranged along a narrow edge direction in a same plane.

Furthermore, in the present invention, the electron emission zones in a number of N may separately emit electrons from each other, and generate X-rays at a number of N positions on the anode which correspond to the electron emission zones, thereby forming N target spots.

Furthermore, in the present invention, from the electron emission zones in a number of N, every n neighboring electron emission zones may be grouped in a non-overlapping manner. The electron emission may be executed by group. X-rays may be generated from the corresponding N/n positions on the anode, which form N/n target spots.

Furthermore, in the present invention, from the number of N electron emission zones, every n neighboring electron emission zones are grouped with “a” (number a) of them overlapped. The electron emission is executed by group. X-rays can be generated from the corresponding $$\left[\frac{N-a}{n-a}\right]$$

positions on the anode, which form $$\left[\frac{N-a}{n-a}\right]$$

target spots.

Furthermore, in the present invention, a surface of the electron emission zone may have an arc shape in a width direction, and electrons emitted from all the micro electron emission units in the electron emission zone may focus toward a point along the width direction.

Furthermore, in the present invention, the distributed X-ray source may further comprise focusing devices, which correspond to and have a same number with the electron emission zones and are provided between the electron source and the anode.

Furthermore, in the present invention, the distributed X-ray source may further comprise a collimating device disposed within or outside of the vacuum chamber, which is arranged in an outputting path of X-ray for outputting X-rays in a shape of taper, fan or pen, or multiple parallel X-rays.

Furthermore, in the present invention, the target spots of the distributed X-ray source may be arranged in a circle or an arc.

Furthermore, in the present invention, the target spots of the distributed X-ray source may be arranged in an enclosed rectangle, a polyline or a section of straight line.

Furthermore, in the present invention, the target on the anode may be transmission target, from which the outputted X-rays have the same direction with an electron beam current from the electron source.

Furthermore, in the present invention, the target on the anode may be reflection target, from which the outputted X-rays form an angle of 90 degree with respect to an electron beam current from the electron source.

Furthermore, an aspect of the present invention provides an X-ray transmission imaging system using the X-ray source of the present invention, comprising: at least one X-ray source according to the present invention, which is adapted to generate X-rays to cover a detection area; at least one detector, which is disposed at a side of the detection area opposite to the X-ray source and is adapted to receive X-rays; and a transporting device, which is disposed between the X-ray source and the detector and is adapted to carry a detected object and move the detected object through the detection area.

Furthermore, an aspect of the present invention provides a back scattering imaging system using the X-ray source of the present invention, comprising: at least one X-ray source according to the present invention, which is adapted to generate a number of pen-shape X-ray beams to cover a detection area; and at least one detector, which is disposed at the same side of the detection area with the X-ray source and is adapted to receive X-rays reflected from a detected object.

Furthermore, in the back scattering imaging system of the present invention, there may be provided at least two groups of the X-ray source and the detector, wherein the at least two groups are disposed at different sides of a detected object.

Furthermore, the back scattering imaging system of the present invention may further comprise a transporting device adapted to carry the detected object and move the detected object through the detection area.

Furthermore, the back scattering imaging system of the present invention may further comprise a movement device, which is adapted to move the X-ray source and the detector through an area in which the detected object is provided.

Furthermore, an aspect of the present invention provides an X-ray detection system, comprising: at least two distributed X-ray sources according to the present invention; and at least two groups of detectors corresponding to the X-ray sources. At least one group of the distributed X-ray source and the detector is used for transmission imaging of a detected object, and at least one group of the distributed X-ray source and the detector is used for back scattering imaging of a detected object. An image comprehensive process system is used to comprehensively process the transmission images and the back scattering images, thereby obtaining more characteristic information of the detected object.

Furthermore, an aspect of the present invention provides a real-time image-guided radiotherapy equipment, comprising: a radiotherapy radiation source, for generating radiation beams for radiotherapy of a patient; a multi-leaf collimator, for adjusting shapes of the radiation beams for radiotherapy to adapt to a lesion; a movable bed, for moving and locating the patient to align a position of the radiation beam for radiotherapy with a position of the lesion; at least one diagnostic radiation source, which is an X-ray source according to the present invention, for generating radiation beams for diagnostic imaging to the patient; a planar detector, for receiving the radiation beams for diagnostic imaging; and a control system, for forming a diagnostic image according to the radiation beams received by the planar detector, locating the position of the lesion in the diagnostic image, aligning centers of the radiation beams for radiotherapy with a center of the lesion, and matching the shapes of the radiation beams for radiotherapy of the multi-leaf collimator with a shape of the lesion. The radiotherapy radiation source is a distributed X-ray source that has a circle or rectangle shape and outputs X-rays in a transverse direction, and an axis or a center line of the distributed X-ray source is in line with a beam axis of the radiotherapy radiation source. That is to say, the radiotherapy radiation source and the diagnostic radiation source are located at a same side of the patient According to the present invention, it is possible to provide an electron source which has low control voltage and large intensity of emission current and an X-ray source using the electron source, as well as an imaging system, an X-ray detection system, a real-time image-guided radiotherapy equipment and the like that use the X-ray source.

DETAILED DESCRIPTION

Figure 1:
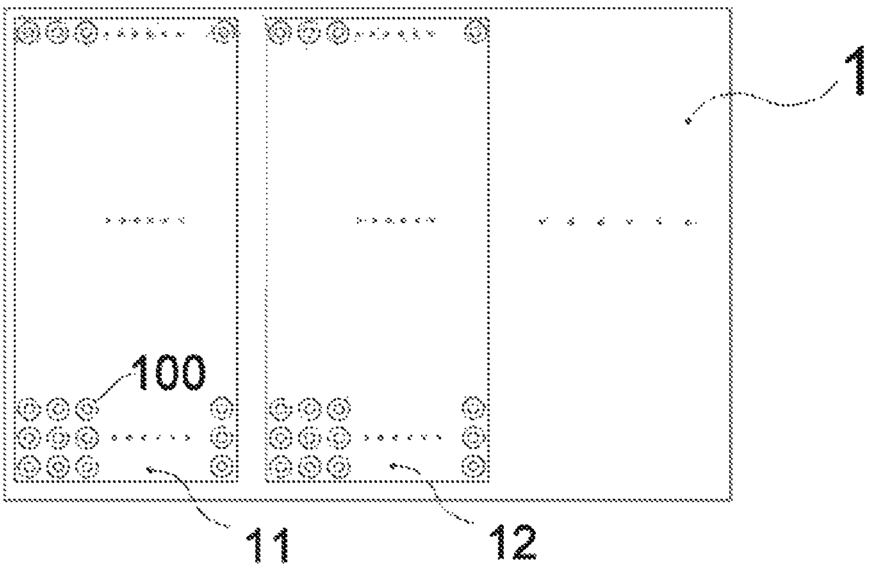
FIG. 1 is a structural schematic diagram of an electron source according to an embodiment of the invention.

Below, the present invention will be explained in detail with reference to the drawings. FIG. 1 is a schematic diagram of a structure of an electron source according to an embodiment of the invention. As shown in FIG. 1, an electron source 1 comprises a plurality of electron emission zones, such as electron emission zones 11, 12, etc. Moreover, although not shown, the electron source 1 may comprise only one electron emission zone. As shown in FIG. 1, each electron emission zone comprises a plurality of micro electron emission units 100. Moreover, the micro electron emission units 100 in one identical electron emission zone are physically (electrically) connected with each other. Different electron emission zones are physically partitioned (i.e., different electron emission zones are electrically isolated from each other). Moreover, in FIG. 1, the plurality of electron emission zones 11, 12 . . . are arranged in a row along a width direction of the electron emission zones (left-right direction as shown in FIG. 1). However, the present invention is not limited thereto. The electron emission zones can also be arranged in other ways, for example arranged in multiple rows, or arranged in multiple rows with electron emission zones in every row staggered with respect to each other. Moreover, sizes and shapes of the electron emission zones and intervals between the electron emission zones can be arbitrarily set as needed.

All the micro electron emission units 100 in one identical electron emission zone can simultaneously emit electrons or do not emit electrons at the same time. The electron emission zones can be controlled to emit electrons at a predetermined sequence, such as, to emit electrons successively, at intervals, alternatively, partially at the same time, group by group, or in other emission ways.

Figure 2:
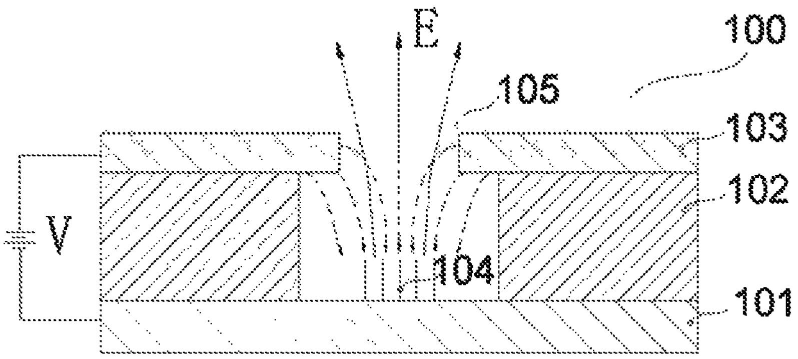
FIG. 2 is a structural schematic diagram showing a micro electron emission unit according to an embodiment of the invention.

FIG. 2 is a structural schematic diagram of a micro electron emission unit 100 according to an embodiment of the invention. As shown in FIG. 2, the micro electron emission unit 100 comprises a base layer 101, an insulating layer 102 on the base layer 101, a grid layer 103 on the insulating layer 102, an opening 105 that penetrates through the grid layer 103 and the insulating layer 102 and reaches the base layer 101, and an electron emitter 104 within the opening 105 fixed at the base layer 101. The base layer 101 is a structural foundation of the micro electron emission unit 100, which provides a structural support and an electric communication (electric connection). The insulating layer 102 is arranged above the base layer 101 and formed from insulating materials to insulate the grid layer 103 from the base layer 101. Moreover, due to the supporting of the insulating layer 102, the distances between the grid layer and the base layer at various locations in one identical electron emission zone are on the whole kept equal (i.e., the surfaces at which the grid layer and the base layer respectively are located are parallel), such that an electric field between the grid layer 103 and base layer 101 is uniform. The grid layer 103 is arranged above insulating layer 102 and formed from metal conductive material. The opening 105 penetrates through the grid layer 103 and the insulating layer 102. The electron emitter 104 is positioned within the opening 105 and connected to the base layer 101. Moreover, the opening 105 may have any processable shape, such as circular, square, polygon, oval and so on, preferably circular. The size (dimension) of the opening 105 within the grid layer 103 can be equal to or different from its size within the insulating layer 102. For example, as shown in FIG. 2, the opening within the insulating layer 102 is slightly larger than that within the grid layer 103. Moreover, the electron emitter 104 is positioned within the opening 105 and connected to the base layer 101. Preferably, the electron emitter 104 is positioned at the center of the opening. The linear length direction of the electron emitter 104 is perpendicular to the surface of the base layer 101. When an external power supply V applies a voltage difference between the grid layer 103 and the base layer 101 (i.e., a field emission voltage), an electric field is generated between the grid layer 103 and the base layer 101. When the intensity of the electric field reaches a certain level, for example over 2V/μm, the electron emitter 104 generates field emission, wherein a generated electron beam current E penetrates the insulating layer 102 and the grid layer 103 and then exits from the opening 105.

Moreover, the electron emitter 104 has a structure containing "nano-materials". The "nano-materials" describe, in a three dimensional space, materials of which at least one dimension is sized in a nanoscale (1~100 nm) or materials composed of basis units at the nanoscale. The "nano-materials" comprise metal or nonmetal nano-powder, nano-fiber, nano-film, nano-bulk and the like. Typical examples of the "nano-materials" comprise carbon nano-tube, zinc oxide nano-wire and so on. Preferably, the nano-materials in the present invention are single-walled carbon nano-tubes and double-walled carbon nano-tubes with a diameter of less than 10 nanometers.

Figure 3:
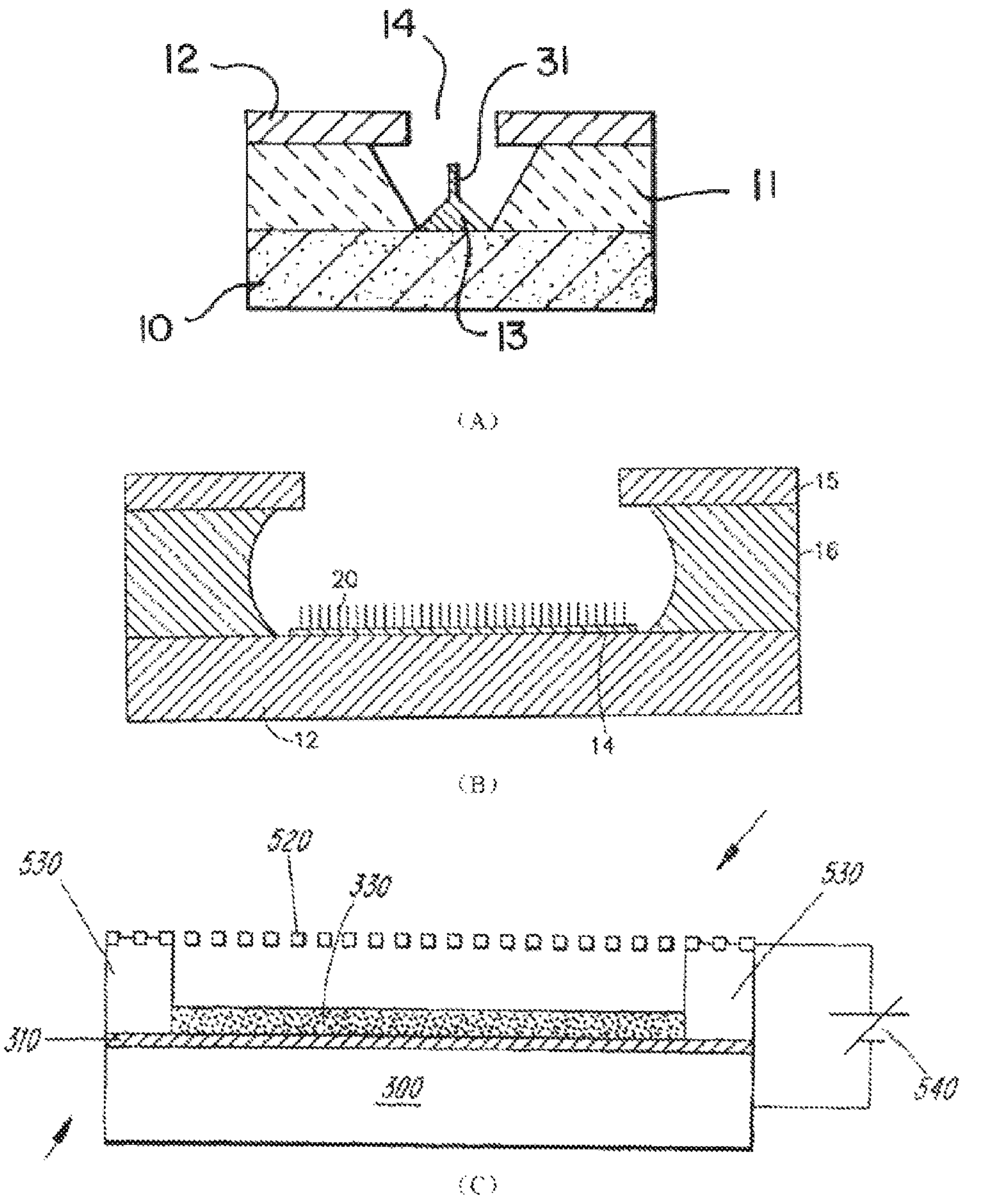
FIG. 3 is a schematic diagram showing in its parts (A)~(C) the structures of several existing field emission units.

After studying and analyzing the Patent References 2~4, the inventor of the present invention realizes that, the electron emission units represented by parts (A) and (B) of FIG. 3 generally have planar array arrangements, in which strip-shaped base layers and grid layers (or complex multi-level grid layers) are vertically and horizontally (or longitudinally and latitudinal) arranged. Each emission unit is independently controlled, and has a very small emission current. In applications, structural proportions of various components are not considered, and thus the quality of emission current is poor. In the structure shown in the part (B) of FIG. 3, the opening size of the grid layer is considerably larger than the distance from the nano-material to the grid layer, and thereby the edge of the nano-material will experience a strong electric field. The edge of the nano-material will first start current emission. However, the emitted current has large divergence angles at its edges, and thus has poor forward characteristics and will be easily blocked and absorbed by the grid layer. The middle part of the nano-material was supposed to generate emission current having good forward characteristics. However, since the electric field experienced by this part is weak, there is no or little emission current. The electron emission units represented by part (C) of FIG. 3 are definitely used in X-ray sources. There is a parallel planar structure between the grid plane and the nano-material plane, which has a large span and a small gap. Due to restrictions in terms of machining precision and installation accuracy, it is hard to make the gap less than 200 μm. Otherwise, two planes will not be parallel and thus the electric field will not be uniform; or a deformation of the grid itself or a deformation resulted from the electric force will substantially affect the uniformity of the electric field, even causing short circuit between the grid and the nano-material. Due to a large gap between the grid plane and the nano-material plane, such electron emission unit causes the control voltage for field emission get higher, which makes it more difficult to control and increase production cost. As compared to the existing structures shown in the parts (A), (B) and (C) of FIG. 3, the present invention provides a better electron emission characteristics and a larger electron beam current E through specific structures and ratios of various components of the micro electron emission unit 100 and the electron emission zones, while reducing the control voltage V required for field emission.

Figure 4:
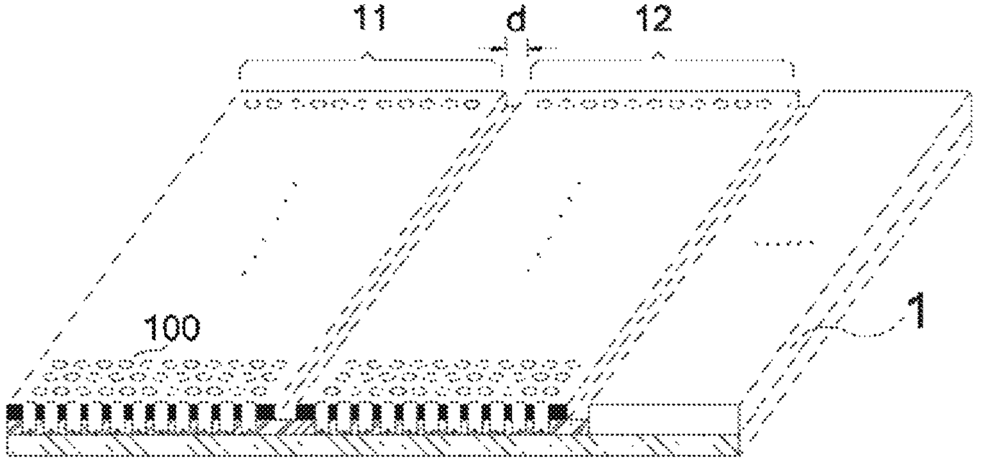
FIG. 4 is a diagram that schematically shows a section view of a front side of an electron source according to an embodiment of the invention.

FIG. 4 is a diagram that schematically shows a section view of a front side of an electron source 1 according to an embodiment of the invention. As shown in FIG. 4, all micro electron emission units 100 in an identical electron emission zone are physically connected (electrically connected). Specifically, for example, base layers 101 of various micro electron emission units 100 are the same substantive layer, grid layers 103 of various micro electron emission units 100 are the same substantive layer, and insulating layers 102 of various micro electron emission units 100 are the same substantive layer. The term "same substantive layer" indicates the respective layers are located at the same spatial level, electrically connected to each other and structurally united together. The insulating layers 102 of various micro electron emission units 100 can also be composed of a plurality of insulating pillars, insulating blocks, insulating strips and so on that are located at the same spatial level, so long as the grid layer 103 and the base layer 101 can be insulated and have the same distances therebetween at various locations (i.e., the grid layer and the base layer are parallel). Moreover, the respective electron emission zones are physically partitioned. Specifically, for example, grid layers 103 of various electron emission zones are independent of and separate from each other, or base layers 101 of various electron emission zones are independent of and separate from each other, or both grid layers 103 and base layers 101 of various electron emission zones are independent of and separate from each other. Accordingly, it is possible that all micro electron emission units in an identical electron emission zone can simultaneously emit electrons or do not emit electrons at the same time, and the respective electron emission zones can be controlled to emit electrons at an independently controlled sequence or a combined controlled sequence. The simultaneous operations of a plurality of micro electron emission units 100 can cause an emission current of an electron emission zone larger than 0.8 mA.

Figure 5:
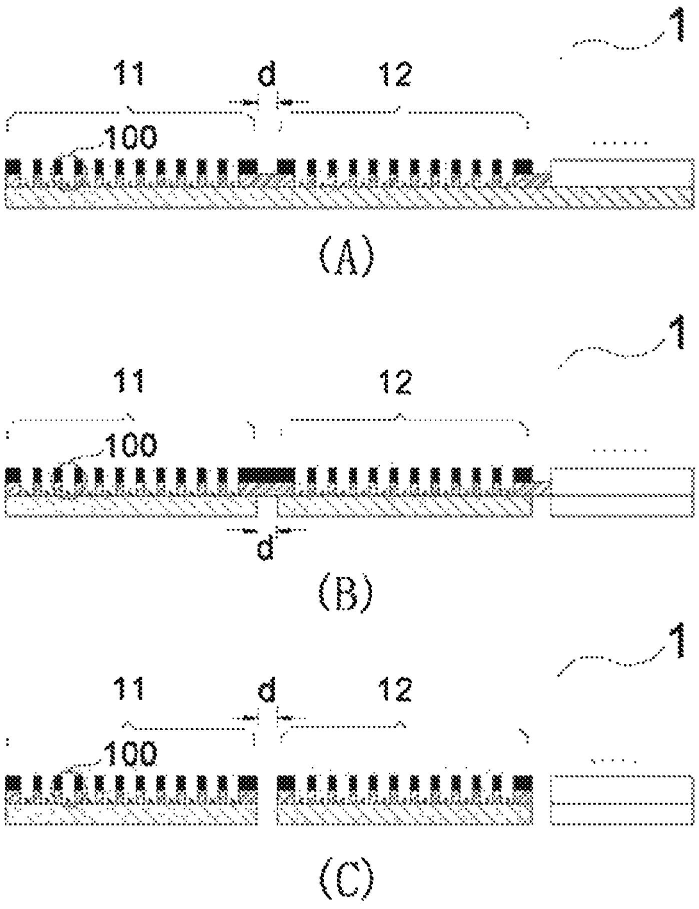
FIG. 5 is a schematic diagram showing in its parts (A)~(C) several electron sources segmented in different ways according to an embodiment of the invention.

FIG. 5 is a schematic diagram showing in its parts (A)~(C) several electron sources segmented in different ways according to an embodiment of the invention. As shown in parts (A), (B) and (C) of FIG. 5, the physical partition between different electron emission zones can be achieved through various specific embodiments. For example, the part (A) of FIG. 5 shows that an electron emission zone 11 and an electron emission zone 12 have a common base layer and a common insulating layer, but their grid layers are separated with a gap d; the part (B) of FIG. 5 shows that an electron emission zone 11 and an electron emission zone 12 have a common grid layer and a common insulating layer, but their base layers are separated with a gap d; and For example, the part (C) of FIG. 5 shows that all of grid layers, insulating layers and base layers of an electron emission zone 11 and an electron emission zone 12 are respectively separated with a gap d.

Moreover, the shape of various electron emission zones can be square, circular, strip shape, oval, polygon, and other combined shapes and so on. The term "rectangle" indicates square or oblong, and the "oblong" means the ratio of its length and width is larger than 1 (for example, 10). Various electron emission zones of one electron source may have the same or different shapes. The various electron emission zones may have the same or different sizes. An electron emission zone can have a macro size of millimeter level, such as from 0.2 mm to 40 mm. The separation gap d between respective electron emission zones may be in a micrometer level, or may have a macro size of millimeter to centimeter level. The separation gaps d between different electron emission zones may be same or different. In a typical structure, each of electron emission zones has a strip shape with a same size of 1 mm×20 mm, these electron emission zones are arranged in a parallel, regular and even way along their short edges (1 mm), and the separation gap d between the various electron emission zones is 1 mm.

Figure 6:
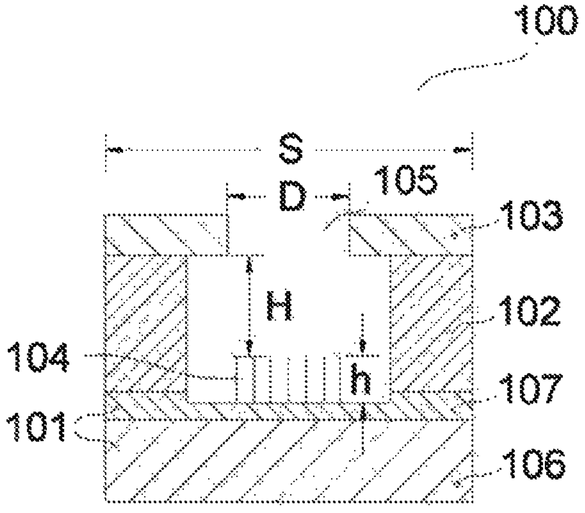
FIG. 6 is a schematic diagram of a detail structure of a micro electron emission unit according to an embodiment of the invention.

FIG. 6 is a schematic diagram of a detail structure of a micro electron emission unit according to an embodiment of the invention. As shown in FIG. 6, in the structure of the micro electron emission unit 100, a base layer 101 provides both structural support and electrical connection, and can be a metal layer or can be composed of a substrate layer 106 and a conducting layer 107. The substrate layer 106 is used to provide structural support, such as providing a smooth surface to which the conducting layer can be adhered. The substrate layer 106 constitutes a structural foundation of the electron emission zone. That is to say, the adhesion, bonding, growth or fixation of the conducting layer 107, the insulating layer 102, the grid layer 103, the electron emitter 104 and so on are based on the substrate layer 106. The substrate layer 106 can comprise metal material, such as stainless steel, or nonmetallic material, such as ceramics. The conducting layer 107 is formed from materials having good conductivity, which can be metal or nonmetallic, such as gold, silver, copper, molybdenum, carbon nano film and so on.

Moreover, a size S of a micro electron emission unit 100 in an electron emission zone along an array arrangement direction can be in a micrometer level. That is to say, a spatial dimension occupied by each micro electron emission unit 100 along the array arrangement direction is ranged from 1 μm to 200 μm, such as typically 50 μm. The direction perpendicular to the array arrangement surface is defined as depth or thickness. The thickness of the substrate layer 106 may have a macro size of millimeter level, such as 1 mm~10 mm, typically for example 4 mm FIG. 6 only shows a portion of the substrate layer 106 along its thickness direction. The thickness of the conducting layer 107 may be at a millimeter level or a micrometer level, and has a certain relation to the material used. For easy manufacture and cost reduction, the thickness of the conducting layer 107 is preferably at a micrometer level, for example a carbon nano film with a thickness of 20 μm. The thickness of the insulating layer 102 may be at a micrometer level, such as from 5 μm to 400 μm, typically for example 100 μm. The thickness of the grid layer 103 may be at a micrometer level, and preferably is close to but smaller than the thickness of the insulating layer 102, such as from 5 μm to 400 μm, typically for example 30 μm. A dimension D of the opening 105 may be at a micrometer level, and may be smaller than the thickness of the insulating layer 102, such as 5 μm to 100 μm, typically for example 30 μm. A height of the electron emitter 104 may be at a micrometer level and smaller than half of the thickness of the insulating layer 102, such as 1 μm to 100 μm, typically for example 20 μm. A distance H from the electron emitter 104 to the grid layer 103 (i.e., the distance from the top of the electron emitter 104 to the lower edge of the grid layer 103) may be at a micrometer level and smaller than the thickness of the insulating layer 102, i.e., smaller than 200 μm, typically for example 80 μm.

The size S of the micro electron emission unit 100 may be at a micrometer level and the size D of the opening 105 may be at a micrometer level, such that a number of single-walled or double-walled carbon nano-tubes or a combination thereof with a diameter of less than 10 nanometers can be arranged within the opening 105, thereby ensuring a certain capability of current emission. The size of the opening 105 is less than the thickness of the insulating layer 102. That is to say, the opening 105 has a shape of "deep well". The distribution of electric field experienced by the top of the electron emitter 104 is relative uniform, such that the emitted current from the electron emitter 104 has relatively well forward characteristic. The thickness of the grid layer 103 is close to but smaller than the thickness of the insulating layer 102, such that the electric field on the top of the electron emitter 104 is relative uniform and there is no significant block of an electron beam current E emitted by the electron emitter 104. The above structures and sizes of the various components improve the quality of the electron beam current E emitted by the micro electron emission unit 100, the intensity of the emission current and the forward characteristics. Moreover, the control voltage is adjusted such that the emission ability of each micro electron emission unit 100 is larger than 100 nA, such as from 100 nA to 25 μA.

Moreover, the distance H from the electron emitter 104 to the grid layer 103 is smaller than 20 μm, such that the control voltage of the grid layer is smaller than 500V (this is because if a ration of a voltage between the grid layer and the electron emitter to the distance between the grid layer and the electron emitter is larger than 2V/μm, the electron emitter will generate field emission. Actually, a nano-material tip of the electron emitter has a great intensity enhancement effect. That is to say, an electric field experienced by the nano-material tip will have a ratio larger than V/H, wherein V is the control voltage of the grid layer, and H is the distance between the grid layer and the electron emitter). Typically, H=80 μm, the control voltage V=300V. Accordingly, the electron source of the present invention can be easily controlled and have a low control cost.

Moreover, the size S of the micro electron emission unit 100 is at a micrometer level. According to above typical size ranges, the size S of the micro electron emission unit 100 may be 50 μm. An electron emission zone with an area of 1 mm×20 mm can contain 8,000 micro electron emission units 100, each of which has an emission ability of 100 nA to 25 μA. The electron emission zone has a current emission ability over 0.8 mA, such as from 0.8 mA to 200 mA.

Figure 7:
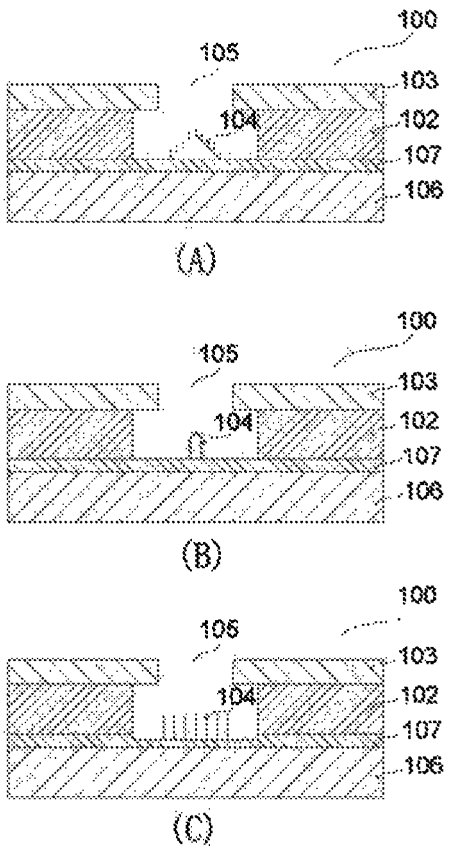
FIG. 7 is a schematic diagram showing in its parts (A)~(C) several micro electron emission units according to an embodiment of the invention, in which nano-materials are fixed in different ways.

Moreover, the electron emitter 104 may be directly fixed on the conducting layer through growth, printing, bonding, sintering and so on, or may be fixed on certain specifically designed bulges on the conducting layer, for example as shown in parts (A), (B) and (C) of FIG. 7. The part (A) of FIG. 7 is a structural schematic diagram that shows a nano-material is fixed on a cone boss fixed. Alternatively, the boss may have a shape of cuboid, cylinder and so on, which are common structures in the art. The part (B) of FIG. 7 shows a structure in which a micro metal pillar (or metal tip) is arranged on the conducting layer and nano-materials are fixed on the metal pillar, thereby forming a tree shape of nano-material. The part (C) of FIG. 7 shows a structure in which the conducting layer is a film formed of a nano-material, and part of nano-material of the nano film within the opening stands up by subsequent process.

Figure 8:
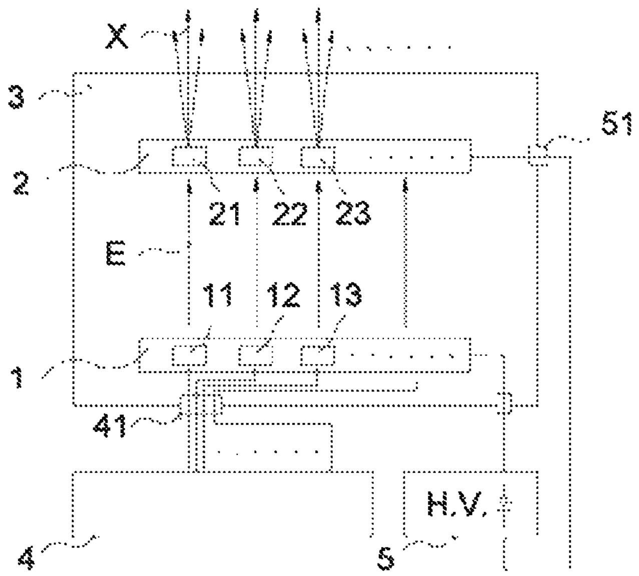
FIG. 8 is a structural schematic diagram of an X-ray source using an electron source according to an embodiment of the invention.

FIG. 8 is a structural schematic diagram of an X-ray source using an electron source according to an embodiment of the invention. The X-ray source shown in FIG. 8 comprises: an electron source 1; an anode 2 arranged opposite to the electron source 1; a vacuum chamber 3 enclosing the electron source 1 and anode 2; an electron source control device 4 connected to the electron source 1; a high voltage power supply 5 connected to the anode 2; a first connection unit 41 penetrating through a housing wall of the vacuum chamber 3 and connected to the electron source 1 and the electron source control device 4; and a second connection unit 51 penetrating through a housing wall of the vacuum chamber 3 and connected to the anode 2 and the high voltage power supply 5.

As discussed above, the electron source 1 comprises at least one electron emission zone. The electron emission zone comprise a plurality of micro electron emission units 100, each of which occupies a spatial size at a micrometer level along the array arrangement direction. The micro electron emission unit 100 comprises a base layer 101, an insulating layer 102 on the base layer 101, a grid layer 103 on the insulating layer 102, an opening 105 that penetrates through the grid layer 103 and the insulating layer 102 and reaches the base layer 101, and an electron emitter 104 within the opening 105 fixed at the base layer 101. The micro electron emission units 100 simultaneously emit electrons or do not emit electrons at the same time.

Furthermore, the operation state of the electron emission zone is controlled by the electron source control device connected to the electron source 1. The electron source control device applies two different voltages to the base layer 101 and the grid layer 103 in the electron emission zone of the electron source 1 through a first connection unit 41. An electric field for field emission is established between the base layer 101 and the grid layer 103, which has a voltage difference V. The intensity of the electric field is V/H (H is a distance between the electron emitter 104 and the grid layer 103). When a voltage of the grid layer 103 is higher than a voltage of the base layer 101, V is positive. Otherwise, V is negative. When the voltage V of the electric field is positive, the nano-material of the electron emitter 104 is carbon nanotube, and the intensity V/H is larger than 2V/μm (due to the intensity enhancement effect of the tip of the nano-material, the real electric field experienced by the nano-material may be larger than the value of V/H), the electron emission zone generates electron emission. When the voltage of the electric field is zero or negative, the electron emission zone does not generate electron emission. If both the voltage V and the intensity V/H increase, the current intensity of the electron emission will get higher. Therefore, the intensity of the current emitted from the electron source 1 may be adjusted through adjusting the output voltage V of the electron source control device 4. For example, an adjustable range of the voltage that can be outputted from the electron source control device 4 is from 0V to 500V. When the output voltage is 0V, the electron source 1 emits no electron. When the output voltage reaches a certain level, for example 200V, the electron source 1 starts emitting electrons. When the output voltage further increases to another level, for example 300V, the current intensity of electrons emitted from the electron source 1 achieves a target value. If the current intensity emitted from the electron source 1 is lower or higher than the target value, turning up or down the output voltage of the electron source control device 4 will cause the current intensity emitted from the electron source 1 back to the target value. This automatic feedback adjustment can be easily achieved in modern control systems. Normally, for convenience of use, the base layer 101 of the electron emission zone of the electron source 1 is connected to ground potential, and a positive voltage is applied to the grid layer 103; or the grid layer 103 is connected to ground potential, and a negative voltage is applied to the base layer 101.

Moreover, the anode 2 is configured to establish a high voltage electric field between the anode 2 and the electron source 1 and receive an electron beam current E which is emitted from the electron source 1 and then accelerated by the high voltage electric field, thereby generating X-rays. The anode 2 is also known as target. Its material usually is high-Z metal materials, which is referred to as target materials. The widely used materials comprise tungsten, molybdenum, palladium, gold, copper, etc. Its material may be a metal or alloy. For cost reduction, a normal metal is usually used as a substrate, on which one or more high-Z materials as target materials are fixed through electroplating, sputtering, high temperature crimping, welding, bonding, etc.

The anode 2 is connected to an anode high voltage power supply 5 through a second connection unit 51. The high voltage power supply 5 can generate a high voltage of dozens of kV to hundreds of kV (for example, 40 kV to 500 kV) which is applied between the anode 2 and the electron source 1. The anode 2 has a positive voltage with respect to the electron source 1. For example, in a typical example, main part of the electron source 1 is connected to ground potential, and a positive high voltage of 160 kV is applied to the anode 2 through the high voltage power supply 5. A high voltage field is formed between the anode 2 and the electron source 1. The electron beam current E emitted from the electron source 1 is accelerated by the high voltage field, moves along an electric field direction (opposite to that of line of electric force), and impinges on the target material of the anode 2, thereby generating X-rays.

Moreover, the vacuum chamber 3 is an all-round hermetic hollow housing, which encloses the electron source 1 and the anode 2. The housing is mainly formed of insulating materials, such as glass, ceramics, etc. Alternatively, the housing of the vacuum chamber 3 can be of metal material, such as stainless steel. When the housing of the vacuum chamber 3 is made of metal materials, a sufficient distance is kept from the housing of the vacuum chamber 3 to the electron source 1 and anode 2 therein. This prevents discharging and electrical spark from occurring between the housing and the electron source 1 or the anode 2, and does not affect an electric field distribution between the electron source 1 and the anode 2. The first connection unit 41 is mounted at a wall of the vacuum chamber 3 to pass electrical cables through the wall of the vacuum chamber 3, while maintaining the sealing of the vacuum chamber 3. The first connection unit 41 is usually a lead terminal made of ceramics. The second connection unit 51 is mounted at a wall of the vacuum chamber 3 to pass electrical cables through the wall of the vacuum chamber 3, while maintaining the sealing of the vacuum chamber 3. The second connection unit 51 is usually a high voltage lead terminal made of ceramics. There is high vacuum within the vacuum chamber 3, which is obtained through drying and venting within a high temperature venting machine. The vacuum level is normally not lower than a level of $10^{-3}$ Pa, preferably not lower than a level of $10^{-5}$ Pa. The vacuum chamber 3 may comprise vacuum maintaining devices, such as ion pump and so on.

Moreover, the electron source 1 comprises at least two electron emission zones, for example N electron emission zones. Each electron emission zone comprises a plurality of micro electron emission units 100. As described above, the micro electron emission unit 100 comprises a base layer 101, an insulating layer 102 on the base layer 101, a grid layer 103 on the insulating layer 102, an opening 105 that penetrates through the grid layer 103 and the insulating layer 102 and reaches the base layer 101, and an electron emitter 104 within the opening 105 fixed at the base layer 101. The micro electron emission units 100 in one identical electron emission zone are physically connected, and different electron emission zones are physically partitioned.

As described above, the feature "the micro electron emission units 100 in one identical electron emission zone are physically connected" means that their base layers 101 are the same substantive layer, their grid layers 103 are the same substantive layer, and their insulating layers 102 are the same substantive layer. The feature "different electron emission zones are physically partitioned" may be the following circumstances. In circumstance (A), the base layers 101 and the insulating layers 102 of different electron emission zones are respectively the same layers, while the grid layers 103 of different electron emission zones are located on a same plane but partitioned. In this case, the base layers 101 of the electron source 1 have a common lead which is connected to the electron source control device 4 through the first connection unit 41. Each of the grid layers 103 of various electron emission zones has a separate lead which is connected to the electron source control device 4 through the first connection unit 41. For a number of N electron emission zones, the first connection unit 41 has at least N+1 separate leads. Moreover, the base layers 101 of the electron source 1 are connected to ground potential of the electron source control device 4 through the common lead, the multiple outputs (all of them having positive voltages) of the electron source control device 4 are connected to the respective grid layers 103 of various electron emission zones through the first connection unit 41, and thereby each electron emission zone can be independently controlled. In circumstance (B), the grid layers 103 and the insulating layers 102 of different electron emission zones are respectively the same layers, while the base layers 101 of different electron emission zones are located on a same plane but partitioned. For example, there is a gap d between neighboring electron emission zones. When the base layer 101 is composed of the non-conductive substrate layer 106 and the conducting layer 107, the partitions of the base layers 101 may be the case of partitions of the conducting layer 107. In this case, the grid layers 103 of the electron source 1 have a common lead which is connected to the electron source control device 4 through the first connection unit 41. Each of the base layers 101 of various electron emission zones has a separate lead which is connected to the electron source control device 4 through the first connection unit 41. For a number of N electron emission zones, the first connection unit 41 has at least N+1 separate leads. Moreover, the grid layers 103 of the electron source 1 are connected to ground potential of the electron source control device 4 through the common lead, the multiple outputs (all of them having positive voltages) of the electron source control device 4 are connected to the respective base layers 101 of various electron emission zones through the first connection unit 41, and thereby each electron emission zone can be independently controlled. In circumstance (C), different electron emission zones are located on the same planes, while the grid layers 103, the insulating layers 102 and the base layers 101 thereof are partitioned. For example, there is a gap d between neighboring electron emission zones. In this case, the base layers 101 and the grid layers 103 of the electron source 1 respectively have common leads which are connected to the electron source control device 4 through the first connection unit 41. For a number of N electron emission zones, the first connection unit 41 has at least 2N separate leads. The multiple outputs (wherein two of the leads compose a group, and there is a voltage difference between them) of the electron source control device 4 are respectively connected to the base layers 101 and the grid layers 103 of various electron emission zones through the first connection unit 41, and thereby each electron emission zone can be independently controlled.

As shown in FIG. 8, a number of N electron emission zones 11, 12, 13 . . . at different locations of the electron source 1 are arranged in a linear manner. The electron source 1 can emit electrons from the different locations. The anode 2 is arranged opposite to the electron source 1. That is, as shown in FIG. 8, the anode 2 is arranged above the electron source 1 and has a same or similar shape and size with those of the electron source 1 respectively, and a surface on which target materials of the anode 2 are provided is opposite to the surface of the grid layers 103 of the electron source 1 in a parallel or substantially parallel manner. The electron beam current E generated from the electron emission zones 11, 12, 13 . . . have a number of N X-ray target spots 21, 22, 23 . . . at different locations on the anode 2. In the present invention, the X-ray source which generates a plurality of X-ray target spots at different locations on an anode will be referred to as a distributed X-ray source.

Figure 9:
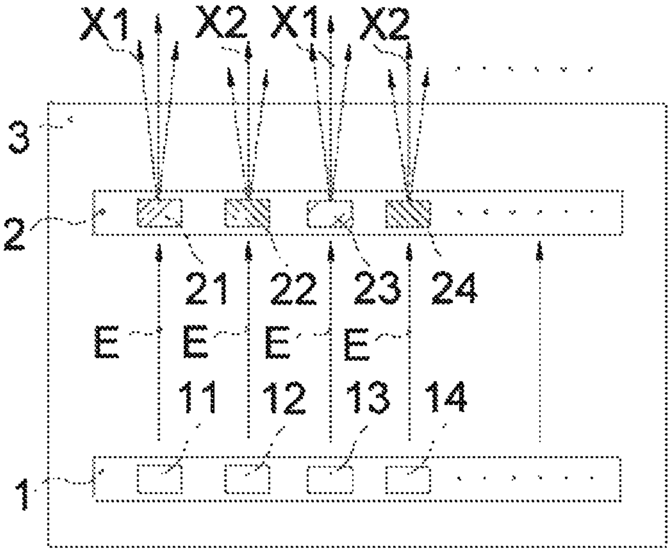
FIG. 9 is a schematic diagram of a distributed X-ray source according to an embodiment of the invention, in which an anode has a plurality of target materials.

FIG. 9 is a schematic diagram of a distributed X-ray source according to an embodiment of the invention, in which an anode has a plurality of target materials. As shown in FIG. 9, the anode 2 of the distributed X-ray source comprises at least two different target materials, and thus can generate X-rays with different comprehensive energies from different target spot locations. X-ray is a continuous spectrum. The term "comprehensive energy" indicates a comprehensive effect reflected when proportions of X-rays with various energies vary. The electron source 1 comprises at least two electron emission zones. The electron beam current emitted from each electron emission zone generates X-ray target spots at different locations on the anode 2. Different target materials are provided at different target spot locations of the anode 2. Since different materials have different characteristic spectrums, X-rays with varying comprehensive energies can be obtained. For example, molybdenum is adopted as substrate of the anode 2, and on the surface of the anode 2 (which is opposite to the electron source 1), a tungsten target of a 200 μm thickness is deposited at the X-ray target spots 21, 23, 25 . . . (which are opposite to the electron emission zones 11, 13, 15 . . . ) and a copper target of a 200 μm thickness is deposited at the X-ray target spots 22, 24, 26 . . . (which are opposite to the electron emission zones 12, 14, 16 . . . ) by ion sputtering. When the X-ray source operates at the same anode voltage, various electron emission zones generate electron beam currents E having same intensity and energy. However, a comprehensive energy of an X-ray X1 generated from the X-ray target spots 21, 23, 25 . . . (tungsten target) is larger than a comprehensive energy of an X-ray X2 generated from the X-ray target spots 22, 24, 26 . . . (copper target).

Figure 10:
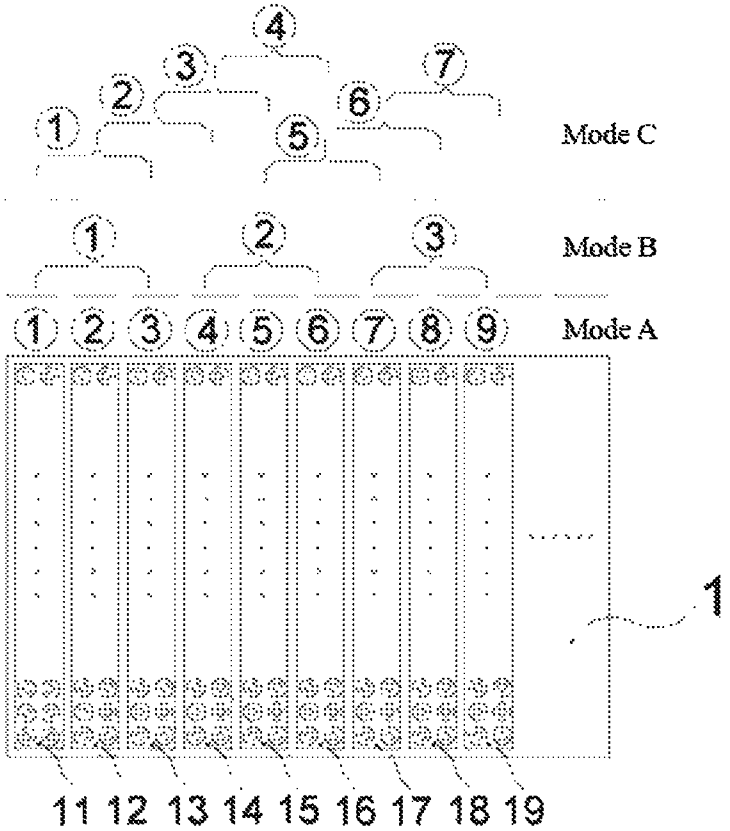
FIG. 10 is a schematic diagram showing three operation modes of a distributed X-ray source according to an embodiment of the invention.

Furthermore, FIG. 10 is a schematic diagram showing three operation modes of a distributed X-ray source according to an embodiment of the invention. As shown in FIG. 10, the distributed X-ray source which uses the electron source 1 according to the present invention has multiple operation modes for achieving various beneficial effects. A typical distributed X-ray source comprises an internal structure in which: the electron emission zones 11, 12, 13 . . . of the electron source 1 have the same strip shapes, and are linearly arranged along a narrow edge direction in the same plane in an even order. When the number of the electron emission zones is large (for example, dozens to thousands), the shape of the electron source 1 is also a strip shape, and the long edge direction of the electron source 1 is perpendicular to the long edge direction of the electron emission zone. The associated anode 2 also has a strip shape, is aligned with the electron source 1 in an up-down direction and is parallel to the electron source 1. The distributed X-ray source can have multiple operation modes for providing various beneficial effects.

The first operation mode is mode A. A number of N electron emission zones 11, 12, 13 . . . independently emit electrons, and generate X-rays from the corresponding N positions on the anode 2 which form N target spots. In a first manner, the electron emission zones, according to their arranged locations, sequentially generate electron beam emission for a certain time T. That is to say, under the control of the electron source control device 4, (1) the electron emission zone 11 emits an electron beam, which generates X-ray emission at the position 21 on the anode 2, and stops the emission after a time period T; (2) the electron emission zone 12 emits an electron beam, which generates X-ray emission at the position 22 on the anode 2, and stops the emission after a time period T; (3) the electron emission zone 13 emits an electron beam, which generates X-ray emission at the position 23 on the anode 2, and stops the emission after a time period T; and so on. When all the electron emission zones have finished the first electron emission, another cycle starts with the above step (1). In a second manner, the electron emission zones that are partly partitioned sequentially generate electron beam emission for a certain time T. That is to say, under the control of the electron source control device 4, (1) the electron emission zone 11 emits an electron beam, which generates X-ray emission at the position 21 on the anode 2, and stops the emission after a time period T; (2) the electron emission zone 13 emits an electron beam, which generates X-ray emission at the position 23 on the anode 2, and stops the emission after a time period T; (3) the electron emission zone 15 emits an electron beam, which generates X-ray emission at the position 25 on the anode 2, and stops the emission after a time period T; . . . and so on until the terminal end of the electron source has been reached. Then, this part of the electron emission zones may emit once again, or other part of the electron emission zones (12, 14, 16 . . . ) may emit concurrently. This process circulates. In a third manner, some of the electron emission zones are grouped together. The various groups sequentially generate electron beam emission for a certain time T. That is to say, under the control of the electron source control device 4, (1) the electron emission zones 11, 14 and 17 emits electron beams, which generates X-ray emission at the positions 21, 24 and 27 on the anode 2, and stops the emission after a time period T; (2) the electron emission zones 12, 15 and 18 emits electron beams, which generates X-ray emission at the positions 12, 15 and 18 on the anode 2, and stops the emission after a time period T; (3) the electron emission zones 13, 16 and 19 emits electron beams, which generates X-ray emission at the positions 23, 26 and 29 on the anode 2, and stops the emission after a time period T; . . . and so on until all the groups finished electron emission. This process circulates. In the mode A, each electron emission zone is independently controlled and generates a separate target spot that corresponds to the electron emission zone. Each electron emission zone has a large width, for example a width of 2 mm, and has a large emission current, for example larger than 1.6 mA. Neighboring electron emission zones have a large gap, for example d=200, which corresponds to targets that have large gaps (for example, centre distance may be 2+2=4 mm) and definite positions. Therefore, it can be easily controlled and used.

The second mode is mode B. From a number of N electron emission zones 11, 12, 13 . . . , every n neighboring electron emission zones are grouped in a non-overlapping manner. The electron emission is executed by group. X-rays can be generated from the corresponding N/n positions on the anode 2, which form N/n target spots. For example, the electron emission zones (11, 12, 13) form group (1), the electron emission zones (14, 15, 16) form group (2), the electron emission zones (17, 18, 19) form group (3) . . . and so on. The newly formed N/3 (N/n=N/3) groups (1), (2), (3) . . . can operate according to any of the operation manners of mode A. The mode B can provide several beneficial effects. On one side, the combination of the electron emission zones increases the intensity of the emission current, and the intensity of X-ray at each target spot is increased simultaneously. The number n may be set according to specific applications of the distributed X-ray source to obtain a desired emission intensity of electron beam. On the other side, the width of each electron emission zone may be further reduced, and more electron emission zones may be grouped together. When a certain electron emission zone malfunctions (for example, a certain micro electron emission unit shorts) and then is eliminated from the group, the group can still operate with the emission current reduced by 1/n. Such reduction can be compensated through parameter adjustment. Therefore, the distributed X-ray source as a whole still has N/n target spots, and there is no "black spot" (similar to black line on monitors) caused by malfunction of some electron emission zone. Avoidance of "black spot", on one side, can prevent blindness of X-ray target spots and thus reduce occurrence of malfunction. On the other side, if a few electron emission zones malfunction due to premature "failure", the means for avoiding "black spot" actually extends the life of the distributed X-ray source. Moreover, the group number n in this mode can be a fixed or unfixed value. For example, the number of electron emission zones in a group may be 3, 5 and so on. The symbol "N/n" merely indicates that the group number and the target spot number is obtained through dividing the number N of the electron emission zones by the group factor n.

The third mode is mode C. From a number of N electron emission zones 11, 12, 13 . . . , every n neighboring electron emission zones are grouped with "a" (number a) of them overlapped. The electron emission is executed by group. X-rays can be generated from the corresponding $$\left[\frac{N-a}{n-a}\right]$$

positions on the anode, which form $$\left[\frac{N-a}{n-a}\right]$$

target spots. The symbol $$\left[\frac{N-a}{n-a}\right]$$

indicates to round the result of $$\frac{N-a}{n-a}$$

to an integer. For example, when n=3 and a=2, the electron emission zones (11, 12, 13) form group (1), the electron emission zones (14, 15, 16) form group (2), the electron emission zones (17, 18, 19) form group (3) . . . and so on. Accordingly, there are formed N−2 groups (1), (2), (3) . . . which can operate according to any of the operation manners of mode A. The mode C can provide several beneficial effects. On one side, the mode C has the same advantages as the mode B, i.e., increasing of the intensity of the emission electron beam current and avoidance of "black spot" of the target spots due to malfunction of some electron emission zones. On the other side, as compared to the mode B, the mode C has more target spots and smaller center distance between the target sports (neighboring target spots, corresponding to the groups of the electron emission zones, are partly overlapped). This is beneficial to the application of the distributed X-ray source, since both the number of the target spots and the number of the views are increased, which can substantially improve the image quality of the imaging system of the distributed X-ray source. As with the mode B, the factors n and "a" can be unfixed values. The symbol $$\text{“}\left[\frac{N-a}{n-a}\right]\text{”}$$

merely indicates a calculation method, which means the number of the target spots in mode C is smaller than that in mode A but larger than that in mode B, which provides an advantage that its electron emission current is larger than that of the mode A and the "black spot" can be avoided.

The symbol N is a positive integer (N≥3), the symbol n is a positive integer (N>n≥2) and the symbol "a" is a positive integer (n>a≥1).

Furthermore, the operation modes of the X-ray source of the present invention are not limited to the above three modes. Any mode is available, as long as the electron emission zones of the electron source 1 can emit electrons in a predetermined sequence or a preset number of neighboring electron emission zones of the electron source 1 can emit electrons in a predetermined sequence.

Furthermore, the above arrangement of the electron emission zones of the electron source 1 is only an exemplary specific structure. However, the arrangement of the electron emission zones may be arrangements of other shapes, irregular arrangements, non-even arrangements, multi-dimensional arrangements (for example, an array of 4×100), non-coplanar arrangements, etc. All of them are embodiments of the electron source 1 of the present invention. The associated anode 2 has a structure and shape that match with the arrangement of the electron emission zones. For example, patent documents such as CN203377194U, CN203563254U, CN203590580U and CN203537653U have disclosed many arrangements. The electron emission zones of the present invention can also be arranged according to the manners disclosed in the above patent documents.

Figure 11:
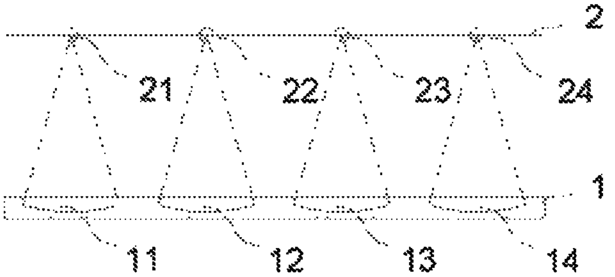
FIG. 11 is a schematic diagram showing a distributed X-ray source in which an electron source has a specific structure according to an embodiment of the invention.

FIG. 11 is a schematic diagram showing a distributed X-ray source according to an embodiment of the invention, in which an electron source has a specific structure. As shown in FIG. 11, the electron emission zones of the electron source 1 have macro widths, for example from 2 mm to 40 mm, which is in a similar order of magnitude to the distance from the electron source 1 to the anode 2. For example, the ratio of the distance between the electron source 1 and the anode 2 to the width of the electron emission zone is less than 10. The surface of the electron emission zones has an arc shape in the width direction (the left-right direction in FIG. 11). Therefore, the electrons emitted from various micro electron emission units 100 in the electron emission zone have a better focusing effect. The surface arc of the electron emission zone may be provided to centre the target position on the associated anode 2. For example, the electron beam current E emitted from the electron emission zone 11 generates the target spot 21 on the anode 2, and the surface of the electron emission zone 11 (or the section thereof) is shown in the width direction as an arc the center of which is located at the target spot 21.

Figure 12:
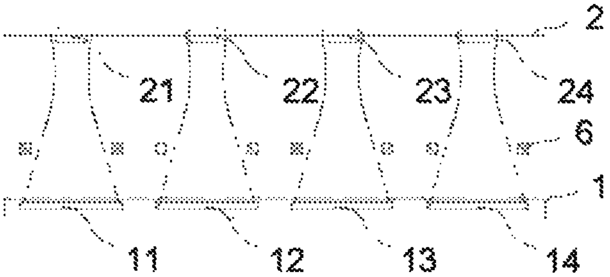
FIG. 12 is a schematic diagram of a distributed X-ray source having a focusing device according to an embodiment of the invention.

FIG. 12 is a schematic diagram of a distributed X-ray source having a focusing device according to an embodiment of the invention. As shown in FIG. 12, the distributed X-ray source further comprises a plurality of focusing devices 6 between the electron source 1 and the anode 2, which are arranged to correspond to the electron emission zones. The focusing device 6 may be such as an electrode, a solenoid that can generate magnetic field, or the like. When the focusing device 6 is an electrode, it can be connected to an external power supply (or control system, not shown) through a focusing cable and connecting means (not shown) to obtain a pre-applied voltage (electric potential), such that the electrons generated from the micro electron emission units 100, when passing through the focusing device 6, will be focused toward the center. When the focusing device 6 is an electrode, it may be an electrode insulated from other components. When the various micro electron emission units 100 emit electrons, a portion of electrons generated from the micro electron emission units 100 at edges of the electron emission zone will be captured by the focusing electrode to form an electrostatic accumulation, thereby an electrostatic field will generate a pushing force to focus the subsequent electrons that pass through the focusing device 6 toward the center. When the focusing device 6 is a solenoid, it can be connected to an external power supply (or control system, not shown) through a focusing cable and connecting means (not shown). Accordingly, when a predetermined electric current flows through the solenoid and then a focusing magnetic field with a predefined intensity is generated above the emission zone, the electrons generated from the micro electron emission units 100, when passing through the focusing device 6, will be focused toward the center. In the present invention, the focusing devices are characterized in that they are arranged with respect to the electron emission zones in a one-to-one correspondence, and enclose all the micro electron emission units 100 in the electron emission zone from above. The focusing cable, connecting means, external power supply (or control system) not shown in FIG. 11 are customary means in the art.

Figure 13:
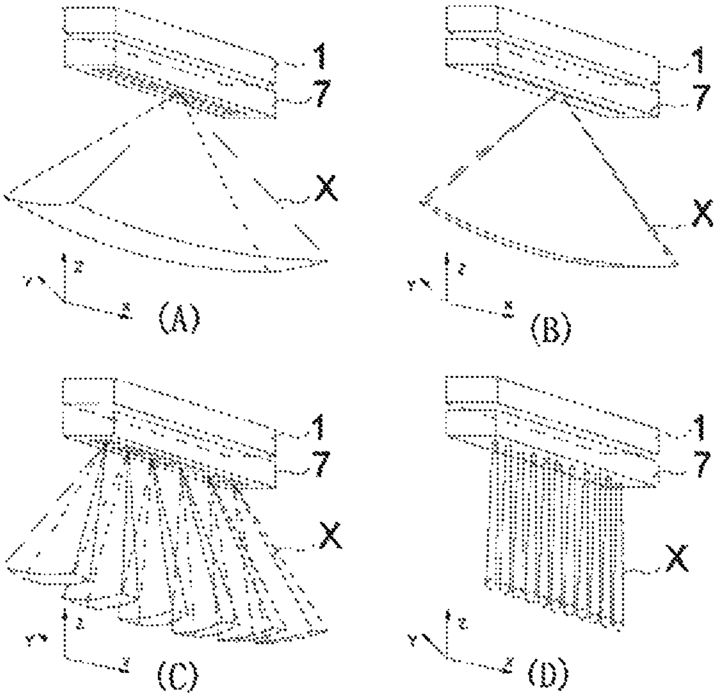
FIG. 13 is a schematic diagram showing in its parts (A)~(D) several collimation effects of a distributed X-ray source according to an embodiment of the invention.

FIG. 13 is a schematic diagram showing in its parts (A)~(D) several collimation effects of a distributed X-ray source according to an embodiment of the invention. As shown in FIG. 13, the distributed X-ray source further comprises a collimating device 7, which is disposed in an output path of X-ray for outputting X-rays in a shape of taper, fan or pen, or multiple parallel X-rays. The collimating device 7 may be an inner collimator mounted within the distributed X-ray source, or an outer collimator mounted outside of the distributed X-ray source. The materials of the collimating device 7 are generally high density metal materials, for example one or more of tungsten, molybdenum, depleted uranium, lead, steel, etc. For ease of description, a coordinate system is defined, in which a length direction of the distributed X-ray source (a target arrangement direction) is X direction, a width direction of the distributed X-ray source is Y direction, and an X-ray outputting direction is Z direction. As shown in the part (A) of FIG. 13, the collimating device 7 is provided in the front of the distributed X-ray source (along the X-ray outputting direction). In the collimating device 7, there are provided collimating slits with large widths. The arrangement length of the collimating slit approximates to the target distribution length of the distributed X-ray source. The collimating device 7 outputs taper X-ray beams each of which has a very large angle in the X direction and a large angle in the Y direction (the part (A) of FIG. 13 only shows a taper X-ray beam generated from a center target spot). As shown in the part (B) of FIG. 13, the collimating device 7 is provided in the front of the distributed X-ray source. There are very narrow X-ray collimating slits in the collimating device 7. The arrangement length of the collimating slit approximates to the target distribution length of the distributed X-ray source. The collimating device 7 outputs X-ray beams each of which has a fan shape in the X-Z plane and a very small thickness in the Y direction (the part (B) of FIG. 13 only shows a fan-shaped X-ray beam generated from a center target spot). As shown in the part (C) of FIG. 13, the collimating device 7 is provided in the front of the distributed X-ray source. The X-ray collimating slits in the collimating device 7 are a series of slits that are arranged in corresponding to the target spot arrangement and each has a width (in the Y direction). The arrangement length of the collimating slit approximates to the target distribution length of the distributed X-ray source. The collimating device 7 outputs an array of X-ray beams each of which has a divergence angle in the Y direction and a thickness in the X direction, wherein the X-ray beams are seen as multiple parallel X-ray beams in the X-Z plane. As shown in the part (D) of FIG. 13, the collimating device 7 is provided in the front of the distributed X-ray source. The X-ray collimating slits in the collimating device 7 are a series of small apertures that are arranged in corresponding to the target spot arrangement. The arrangement length of the collimating slit approximates to the target distribution length of the distributed X-ray source. The collimating device 7 outputs an array of X-ray spot-beams in the X-Y plane, each of which is a pen-shaped X-ray beam that is coaxial with the Z-direction. All the collimating devices 7 shown in the parts (A), (B), (C) and (D) of FIG. 13 are provided outside of the X-ray source, and are used to modify the shapes of the X-ray beams in the outputting path for X-ray. However, the collimating device 7 can also be mounted within the X-ray source, i.e., between the anode 2 and the vacuum chamber 3. The collimating device 7 may be mounted closer to the anode 2 or the wall of the vacuum chamber 3. In this case, the collimating device 7 is also used to modify the shapes of the X-ray beams in the outputting path for X-ray. When the collimating device is mounted within the X-ray source, a reduction in size and weight can be achieved, and sometimes a better collimating effect is also obtained.

Figure 14:
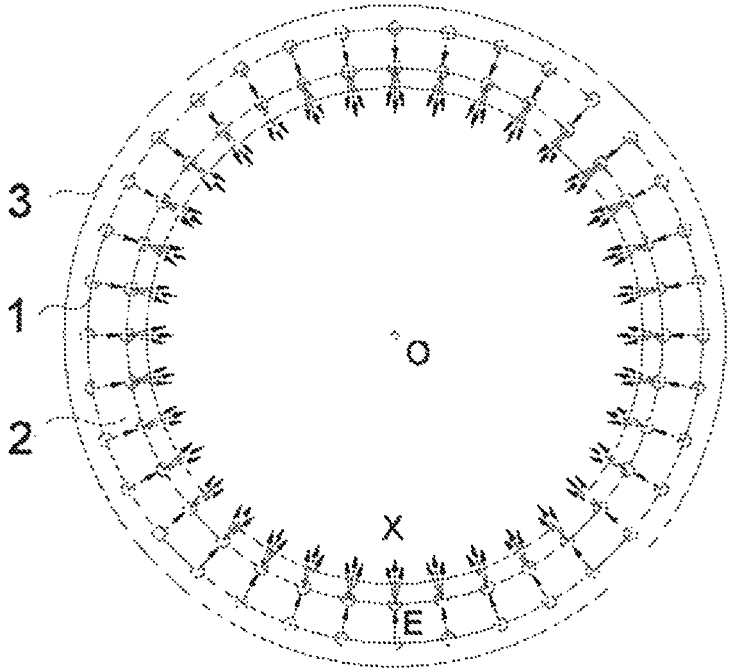
FIG. 14 is a schematic diagram of a distributed X-ray source in a circular shape according to an embodiment of the invention.

FIG. 14 is a schematic diagram of a distributed X-ray source in a circular shape according to an embodiment of the invention. As shown in FIG. 14, the target spots of the distributed X-ray source are arranged in a circle or a section of an arc. FIG. 14 shows a case where the shape of the distributed X-ray source is a circle. Various electron emission zones of the electron source 1 are arranged in a circle, and the associated anodes 2 are also arranged in a circle. The vacuum chamber 3 is provided as a circular ring that encloses the electron source 1 and the anodes 2, the center of which is denoted as "O". The generated X-rays point to the center O or an axis in which the center O is positioned. The shapes of the distributed X-ray source can also be oval, three-quarter circle, semicircle, quarter circle, an arc subtending other angles, etc.

Figure 15:
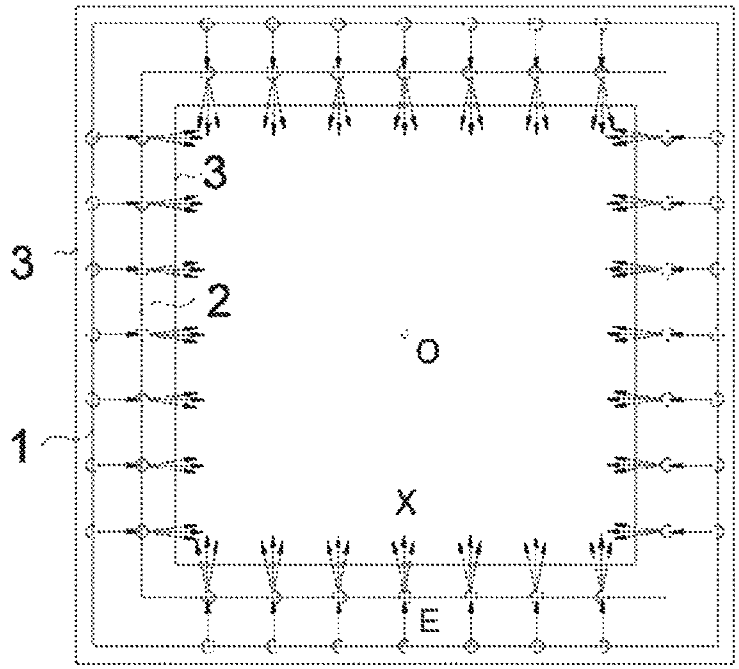
FIG. 15 is a schematic diagram of a distributed X-ray source in a box shape according to an embodiment of the invention.

FIG. 15 is a schematic diagram of a distributed X-ray source in a box shape according to an embodiment of the invention. As shown in FIG. 15, the target spots of the distributed X-ray source are arranged in an enclosed rectangle, a polyline or a section of a straight line. FIG. 15 shows a case where the shape of the distributed X-ray source is a rectangular frame. Various electron emission zones of the electron source 1 are arranged in a rectangular frame, and the associated anodes 2 are also arranged in a rectangular frame. The vacuum chamber 3 is provided as a rectangular frame that encloses the electron source 1 and the anodes 2. The generated X-rays point to the inside of the rectangular frame. The shapes of the distributed X-ray source can also be U-shape (three-quarter rectangle), L-shape (half a rectangle), straight line (quarter rectangle), equilateral polygon, other non-right-angle polylines, etc.

Figure 16:
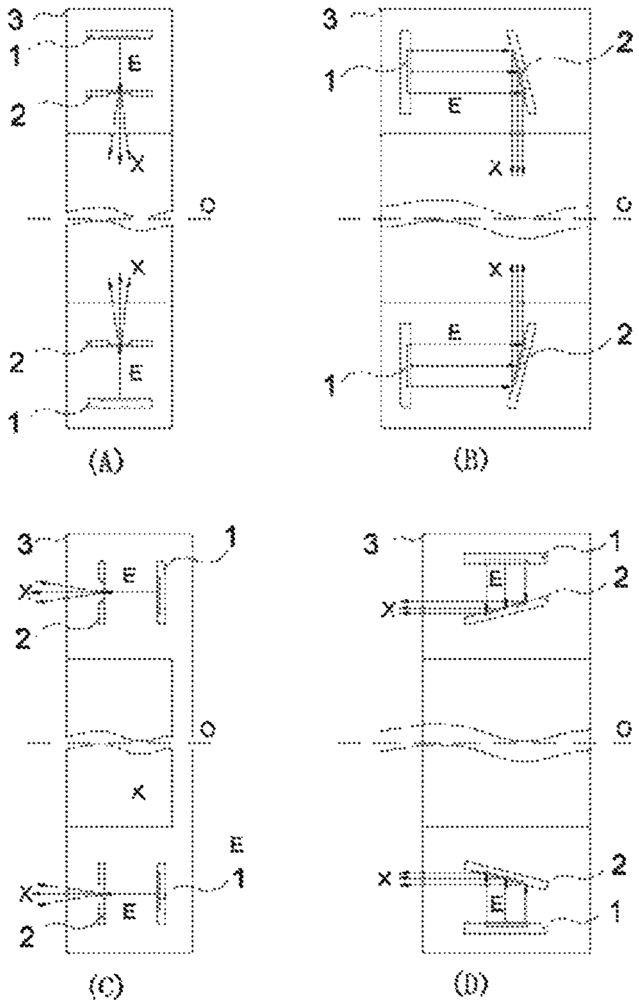
FIG. 16 is a schematic diagram showing in its parts (A)~(D) several section views of a distributed X-ray source according to an embodiment of the invention.

FIG. 16 is a schematic diagram showing in its parts (A)~(D) several section views of a distributed X-ray source according to an embodiment of the invention. As shown in FIG. 16, the targets on the anode 2 of the distributed X-ray source may be transmission target or reflection target.

The part (A) of FIG. 16 shows a case where the anode targets of the distributed X-ray source are transmission targets. That is to say, in this case, the outputting direction of the X-ray is substantially same with the incoming direction of the electron beam current E. In connection with FIG. 14, the part (A) of FIG. 16 may be interpreted that: various electron emission zones of the electron source 1 are arranged in an outer circle, and the surfaces of the electron emission zones are parallel to the axis of the circle; various target spots of the anodes 2 are arranged in an inner circle, which is concentric with the outer circle; the vacuum chamber 3 is a hollow circular ring that encloses the electron source 1 and the anode 2; there is provided a thin thickness at the target locations of the anode 2, for example less than 1 mm; and the directions of the electron beam current E and the X-ray both point to the center O of the circle. In connection with FIG. 15, the part (A) of FIG. 16 may be interpreted that: various electron emission zones are arranged in an outer rectangle, and the surfaces of the electron emission zones are parallel to a center axis of the rectangle; various target spots of the anodes 2 are arranged in an inner rectangle, the center of which coincides with that of the outer rectangle; the vacuum chamber 3 is a hollow rectangular ring that encloses the electron source 1 and the anode 2; there is provided a thin thickness at the target locations of the anode 2, for example less than 1 mm; and the directions of the electron beam current E and the X-ray both point to the inside of the rectangles.

The part (B) of FIG. 16 shows a case where the anode targets of the distributed X-ray source are reflection targets. That is to say, in this case, an angle of 90 degrees is formed between the outputting direction of the X-ray and the incoming direction of the electron beam current E (the angle of 90 degrees herein includes an angle of about 90 degree, wherein the angle range may be from 70 to 120 degree, preferably from 80 to 100 degree). In connection with FIG. 14, the part (B) of FIG. 16 may be interpreted that: various electron emission zones of the electron source 1 are arranged in a circle, and the surfaces of the electron emission zones are perpendicular to an axis O of the circle; various target spots of the anodes 2 are arranged in another circle, wherein the two circles have the same size and their centers are located at the circle axis, and planes at which the above two circles are provided are parallel to each other; or furthermore, the anode 2 has an inclined angle (for example, 10 degree) with respect to the electron source 1 such that a surface in which the various target spots of the anode 2 are arranged is a conical surface, an axis of which coincides with the circle axis. The vacuum chamber 3 is a hollow circular ring that encloses the electron source 1 and the anode 2. The direction of the electron beam current E is parallel to the circle axis, and the direction of the X-ray points to the center O of the circle. In connection with FIG. 15, the part (B) of FIG. 16 may be interpreted that: various electron emission zones are arranged in a rectangle, and the surfaces of the electron emission zones are parallel to a center axis O of the rectangle; various target spots of the anodes 2 are arranged in another rectangle, wherein the two rectangles have the same size and planes at which the two rectangles are provided are parallel to each other; or furthermore, the anode 2 has an inclined angle (for example, 10 degree) with respect to the electron source 1 such that a surface in which the various target spots of the anode 2 are arranged is a pyramid surface, a center line of which coincides with that of the rectangles. The vacuum chamber 3 is a hollow rectangular ring that encloses the electron source 1 and the anode 2. The direction of the electron beam current E is parallel to the center line of the rectangle, and the direction of the X-ray points to the inside of the rectangle.

Furthermore, a light source shown in the part (C) of FIG. 16 is also a transmission target. As compared to the part (A) of FIG. 16, the difference is only in the arrangements of the electron source 1 and the anode 2 in the circle (or rectangle), i.e., replacing outer-inner circles (or outer-inner rectangles) by front-back circles (or front-back rectangles). The directions of the electron beam current E and the X-ray both are parallel to the axis of circle (or the center line of rectangle). That is to say, the distributed X-rays are emitted in a transverse direction of the circle (or a transverse direction of the rectangle).

Furthermore, a light source shown in the part (D) of FIG. 16 is also a reflection target. As compared to the part (B) of FIG. 16, the difference is only in the arrangements of the electron source 1 and the anode 2 in the circle (or rectangle), i.e., replacing outer-inner circles (or outer-inner rectangles) by front-back circles (or front-back rectangles). The direction of the electron beam current E is perpendicular to the center line of the circle (or the center line of the rectangle), and the direction of the X-ray is parallel to the axis of circle (or the center line of rectangle). That is to say, the distributed X-rays are emitted in a transverse direction of the circle (or a transverse direction of the rectangle).

Strictly speaking, only the part (A) of FIG. 16 corresponds to FIG. 14 and FIG. 15, while the part (B) of FIG. 16 corresponds to FIG. 14. By making reference to the description of FIG. 15, it is convenient to explain the part (B) of FIG. 16.

Moreover, the shape of the distributed X-ray source may be a combination of the above described curves and strait lines, or spiral and the like, any of which is processable for modern processing technology.

Figure 17:
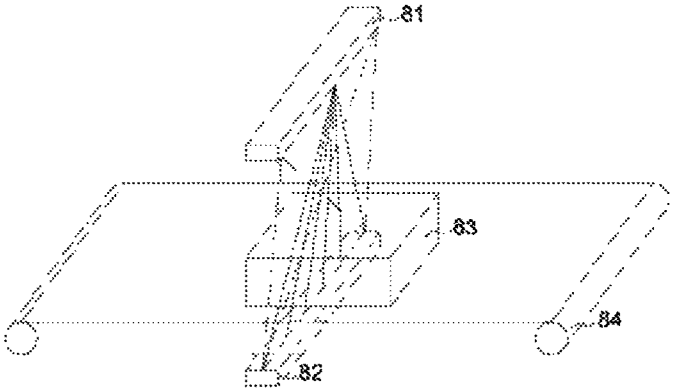
FIG. 17 is a schematic diagram of an X-ray transmission imaging system using a distributed X-ray source according to an embodiment of the invention.

FIG. 17 is a schematic diagram of an X-ray transmission imaging system using a distributed X-ray source according to an embodiment of the invention. FIG. 17 shows the transmission imaging system using the distributed X-ray source of the present invention comprises at least one X-ray source 81 according to the present invention, for generating X-rays able to cover a detection area; at least one detector 82 disposed at other side of the detection area and opposite to the X-ray source 81, for receiving the X-rays; and a transporting device 84 disposed between the X-ray source 81 and the detector 82, for carrying a detected object 83 through the detection area.

A first specific embodiment comprises: one X-ray source, which has one electron emission zone and forms one X-ray target spot; and a plurality of detectors, which form a linear array or a planar array (or a planar detector). This embodiment has a configuration similar to existing X-ray transmission imaging system. This embodiment provides a simple structure, a small size and a low cost. However, the field emission X-ray source of the present invention has advantages of lower control voltage and fast start-up speed.

A second specific embodiment comprises: one X-ray source, which has two electron emission zones, wherein two X-ray target spots have different target materials and can alternately generate two X-ray beams with different energies; and a plurality of detectors, which form a linear array or a planar array (or a planar detector), or serving as dual energy detectors. This embodiment provides a simple structure, a small size and a low cost, and can achieve dual energy imaging, which improves ability to identify materials of detected objects.

A third specific embodiment comprises: one distributed X-ray source, which has a plurality of X-ray target spots; and a plurality of detectors, which form a linear array or a planar array (or a planar detector). These detectors perform transmission imaging to the detected object at different angles (locations), thereby obtaining a transmission image comprising multilevel information in a depth direction. Compared to a multi-view system using a number of normal X-ray source, this embodiment provides a simple structure, a small size and a low cost.

A fourth specific embodiment comprises: one distributed X-ray source, which has a plurality of X-ray target spots; and one or several detectors, which obtains transmission images through a "reverse" imaging principle. This embodiment is characterized in reduction of detector number and cost.

A fifth specific embodiment comprises: one or more distributed X-ray sources and one or more associated detector arrays, wherein all X-ray target spots are arranged to surround the detected object and the surrounding angle is larger than 180 degree. This embodiment provides a large surrounding angle arrangement of static X-ray source to obtain a complete 3D transmission image of the detected object, thereby enabling a fast detection speed and a high efficiency.

A sixth specific embodiment comprises: a plurality of distributed X-ray sources and a plurality of associated detector arrays, which are arranged in a plurality of planes along a delivery direction of the detected object. This embodiment is characterized in improving the detection speed multiply, or forming multi-energy 3D transmission images in different planes with X-rays of different energies, or progressively improving quality of detection images. For example, a first plane roughly detects suspicious areas, a second plane performs a careful detection to the suspicious areas through different parameters, thereby high resolution and sharpness images can be obtained.

Figure 18:
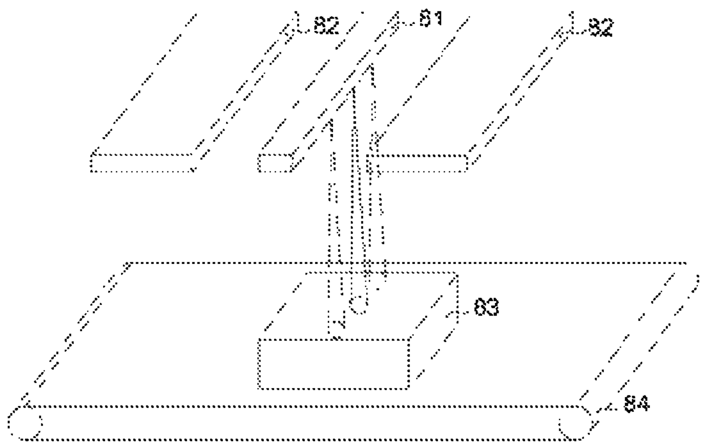
FIG. 18 is a schematic diagram of a back scattering imaging system using a distributed X-ray source according to an embodiment of the invention.

FIG. 18 is a schematic diagram of a back scattering imaging system using a distributed X-ray source according to an embodiment of the invention. FIG. 18 shows the back scattering imaging system using the distributed X-ray source of the present invention comprises: at least one distributed X-ray source 81 according to the present invention, for generating a number of pen-shaped X-ray beams to cover a detection area; and at least one detector 82 disposed at the same side of the detection area and opposite to the X-ray source 81, for receiving the X-rays that are reflected from a detected object.

A first specific embodiment further comprises: a transporting device 84 for carrying the detected object 83 through the detection area to accomplish an overall imaging of the detected object.

A second specific embodiment further comprises: a movement device for moving the distributed X-ray source 81 and the detected object 82 such that the detection area can scan the detected object to accomplish an overall imaging of the detected object.

A third specific embodiment comprises: at least two groups of the distributed X-ray sources 81 and the detectors 82, disposed at different sides of the detected object. By moving the detected object through the transporting device or moving the X-ray source through a movement device, an "all round" imaging of the detected object is accomplished.

Moreover, an X-ray detection system is provided, which comprises: at least two distributed X-ray sources of the present invention; at least two groups of detectors that correspond to the X-ray sources; and an image comprehensive process system. At least one group of the distributed X-ray source and the detector is used to perform a transmission imaging to a detected object. At least one group of the distributed X-ray source and the detector is used to perform a back scattering imaging to the detected object. The image comprehensive process system is used to comprehensively process the transmission images and the back scattering images, thereby obtaining more characteristic information of the detected object.

Furthermore, it should be particularly noted that, the above X-ray transmission imaging system and back scattering imaging system may be common arrangement on ground, or may be integrated into movable devices, for example vehicles, to constitute a movable transmission imaging system and a movable back scattering imaging system.

Furthermore, it should be particularly noted that, the above transmission imaging system and back scattering imaging system have general meanings. By adding auxiliary components or not, the above systems can be used to detect such as small vehicles, freights, luggage, baggage, mechanical components, industry products, personnel, body parts and so on.

Furthermore, a real-time image-guided radiotherapy equipment is provided, which comprises: a radiotherapy radiation source, for generating radiation beams for radiotherapy of a patient; a multi-leaf collimator for adjusting shapes of the radiation beams for radiotherapy to adapt to a lesion; a movable bed for moving and locating the patient such that the position of the radiation beam for radiotherapy aligns with the position of the lesion; at least one distributed X-ray source of the present invention for generating radiation beams for performing a diagnostic imaging to the patient; a planar detector for receiving the radiation beams for diagnostic imaging; a control system, for forming a diagnostic image according to the radiation beams received by the planar detector, locating the position of the lesion in the diagnostic image, aligning centers of the radiation beams for radiotherapy with the center of the lesion, and matching the shapes of the radiation beams for radiotherapy of the multi-leaf collimator with the shape of the lesion. The distributed X-ray source is a distributed X-ray source that has a circle or rectangle shape and outputs X-rays in a transverse direction (the cases shown in the parts (C) and (D) of FIG. 16). The axis or center line of the distributed X-ray source is in line with the beam axis of the radiotherapy radiation source. That is to say, the radiotherapy radiation source and the diagnostic radiation source are located at the same side of the patient. The planar detector is located at the other side of the patient with respect to the diagnostic radiation source. It is possible to perform an image-guided radiotherapy to the patient and obtain the diagnostic image at the same time, without rotating cantilevers of the radiotherapy equipment. This is a "real-time" image-guided radiotherapy. Regarding therapy of body parts having physiological movements, for example lung, heart and so on, the "real-time" image-guided radiotherapy can decrease exposure doses and reduce exposure to normal organics, which is very important. Moreover, the distributed X-ray source of the present invention has a number of target spots and thus can obtain "three-dimensional" diagnostic images having depth information, which differ from normal planar images. In the image-guided radiotherapy, this can further improve the guiding accuracy and locating precision of the radiation beams for radiotherapy.

As described above, the present invention is illustrated, but not limited to this. It should be understood that various combinations and alterations within the spirit of the present invention, and any device, equipment or system that adopts the electron source of the present invention or the X-ray source of the present invention are within the scope of the present invention.

REFERENCE SIGN LIST

1: Electron Source;
11, 12, 13: Electron Emission Zones at Electron Source;
100: Micro Electron Emission Unit;
101: Base Layer;
102: Insulating Layer;
103: Grid Layer;
104: Electron Emitter;
105: Opening;
106: Substrate Layer;
107: Conducting Layer;
2: Anode;
21, 22, 23: X-ray Target Spots at Anode;
3: Vacuum Chamber;
4: Electron Source Control Device;
41: First Connection Unit;
5: High Voltage Power Supply;
51: Second Connection Unit;
6: Focusing Device;
7: Collimating Device;
81: X-ray Source;
82: Detector;
83: Detected Object;
84: Transporting device;
S: Size of Micro Electron Emission Unit;
D: Size of Opening;
H: Distance from Electron Emitter to Grid Layer;
h: Height of Electron Emitter;
d: Interval between Electron Emission Zones;
V: Field Emission Voltage;
E: Electron Beam Current:
X: X-ray;
O: Center, Centerline or Axis of X-ray Source

The invention claimed is:

1. An electron source, comprising:

one or more electron emission zones, each of which comprises a plurality of micro electron emission units;

wherein the micro electron emission unit comprises: a base layer, an insulating layer on the base layer, a grid layer on the insulating layer, an opening in the grid layer, and an electron emitter that is fixed at the base layer and corresponds to a position of the opening; and wherein the micro electron emission units in the same electron emission zone are electrically connected, and simultaneously emit electrons or do not emit electrons at the same time;

wherein the opening has a size that is less than the thickness of the insulating layer, and the opening has a size that is less than a distance from the electron emitter to the grid layer.

2. The electron source according to claim 1, wherein the insulating layer has a thickness less than 200 μm.

3. The electron source according to claim 1, wherein the grid layer is parallel to the base layer.

4. The electron source according to claim 1, wherein the electron emitter has a height that is less than half of a thickness of the insulating layer.

5. The electron source according to claim 1, wherein the electron emitter is formed to comprise nano-materials, and the nano-materials is one of single-walled carbon nano-tubes, double-walled carbon nano-tubes, multi-walled carbon nano-tubes, and any combination of thereof.

6. The electron source according to claim 1, wherein the base layer comprises a substrate layer and a conducting layer on the substrate layer, and the electron emitter is fixed at the conducting layer.

7. The electron source according to claim 6, wherein the electron emitter is composed in a way that: the conducting layer is a film made of nano-materials, and part of nano-material of the nano film at a position corresponding to the opening stands up and is perpendicular to a surface of the conducting layer.

8. The electron source according to claim 1, wherein a spatial size occupied by the micro electron emission unit along an array arrangement direction is ranged from 1 μm to 200 μm.

9. The electron source according claim 1, wherein a ratio of a length to a width of the electron emission zone is larger than 2.

10. The electron source according to claim 1, wherein the electron source comprises at least two different electron emission zones, and wherein the different electron emission zones are electrically partitioned.

11. The electron source according to claim 10 wherein different electron emission zones are electrically partitioned such that: one of the respective base layers of all the electron emission zones are separated from each other, the respective grid layers of all the electron emission zones are separated from each other, and both the respective base layers and grid layers of all the electron emission zones are separated from each other.

12. The electron source according to claim 1, wherein an emission current of each electron emission zone is larger than 0.8 mA.

13. An X-ray source, comprising:

a vacuum chamber;

an electron source disposed within the vacuum chamber, the electron source comprising:

one or more electron emission zones, each of which comprises a plurality of micro electron emission units, wherein the micro electron emission unit comprises: a base layer, an insulating layer on the base layer, a grid layer on the insulating layer, an opening in the grid layer, and an electron emitter that is fixed at the base layer and corresponds to a position of the opening, and wherein the micro electron emission units in a same electron emission zone are electrically connected, and simultaneously emit electrons or do not emit electrons at a same time;

wherein the opening has a size that is less than the thickness of the insulating layer, and the opening has a size that is less than a distance from the electron emitter to the grid layer;

an anode, disposed opposite to the electron source within the vacuum chamber;

an electron source control device, adapted to apply voltage between the base layer and the grid layer of the electron emission zone of the electron source; and a high voltage power supply, connected to the anode and adapted to provide high voltage to the anode.

14. The X-ray source according to claim 13, further comprising:

a first connection unit, mounted at a wall of the vacuum chamber and adapted to connect the electron source and the electron source control device; and a second connection unit, mounted at a wall of the vacuum chamber and adapted to connect the anode and the high voltage power supply.

15. The X-ray source according to claim 13, wherein the anode has target spot locations that correspond to the respective electron emission zones of the electron source, wherein each of a plurality of different target material are provided at respective target spot locations of the anode.

16. The X-ray source according to claim 13, wherein the electron source control device executes a control such that the electron emission zones of the electron source emit electrons in a predetermined sequence.

17. The X-ray source according to claim 13, wherein the electron source control device executes a control such that a preset number of neighboring electron emission zones of the electron source emit electrons in a predetermined sequence.

18. The X-ray source according to claim 13, wherein a surface of the electron emission zone has an arc shape in a width direction, and electrons emitted from all the micro electron emission units in the electron emission zone focus toward a point along the width direction.

19. The X-ray source according to claim 13, further comprising:

a plurality of focusing devices, which correspond to the plurality of electron emission zones respectively and are disposed between the electron source and the anode, wherein the focusing devices enclose all the micro electron emission units in the electron emission zone from above;

wherein the focusing device comprises an electrode or a solenoid.

20. The X-ray source according to claim 13, wherein the target spots on the anode are arranged in a circle, in an arc, in an enclosed rectangle, in a polyline, or in a section of straight line.

* * * * *